US010369221B2

(12) United States Patent
Zhu et al.

(10) Patent No.: US 10,369,221 B2
(45) Date of Patent: Aug. 6, 2019

(54) CONJUGATED PORPHYRIN CARBON QUANTUM DOTS FOR TARGETED PHOTODYNAMIC THERAPY

(71) Applicant: Hong Kong Baptist University, Hong Kong (HK)

(72) Inventors: Xunjin Zhu, Hong Kong (HK); Wai Kwok Wong, Hong Kong (HK); Fengshou Wu, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 0 days.

(21) Appl. No.: 15/806,514

(22) Filed: Nov. 8, 2017

(65) Prior Publication Data

US 2018/0125976 A1    May 10, 2018

Related U.S. Application Data

(60) Provisional application No. 62/419,454, filed on Nov. 8, 2016.

(51) Int. Cl.
| | |
|---|---|
| *A61K 41/00* | (2006.01) |
| *A61K 47/68* | (2017.01) |
| *A61K 47/69* | (2017.01) |
| *G01N 33/58* | (2006.01) |
| *G01N 33/574* | (2006.01) |

(52) U.S. Cl.
CPC ...... *A61K 41/0071* (2013.01); *A61K 47/6849* (2017.08); *A61K 47/6857* (2017.08); *A61K 47/6929* (2017.08); *G01N 33/57423* (2013.01); *G01N 33/57492* (2013.01); *G01N 33/582* (2013.01); *G01N 33/587* (2013.01); *G01N 2333/71* (2013.01)

(58) Field of Classification Search
None
See application file for complete search history.

(56) References Cited

PUBLICATIONS

Yamuna et al. (J Nanopart Res., 15:1399, 2013).*
Bottini et al. (Biomacromolecules, 12:3381-3393, 2011).*
Zheng et al.; Glowing Graphene Quantum Dots and Carbon Dots: Properties, Syntheses, and Biological Applications; Small; 2015; pp. 1620-1636; vol. 11, Issue 14; Wiley.
Zhang et al.; Carbon Dots: Large-Scale Synthesis, Sensing and Bioimaging; Materials Today; 2016; pp. 382-393; vol. 19, Issue 7; Elsevier.
Martindale et al.; Solar Hydrogen Production Using Carbon Quantum Dots and a Molecular Nickel Catalyst; Journal of the American Chemical Society; 2015; pp. 6018-6025; vol. 137, Issue 18; ACS Publications.
Fei et al.; Atomic Cobalt on Nitrogen-Doped Graphene for Hydrogen Generation; Nature Communications; 2015; vol. 6; Article No. 8668; Nature.
Guo et al.; Facile Access to Versatile Fluorescent Carbon Dots toward Light-Emitting Diodes; Chemical Communications; 2012; pp. 2692-2694; vol. 48, Issue 21; The Royal Society of Chemistry.

(Continued)

*Primary Examiner* — Bong-Sook Baek
(74) *Attorney, Agent, or Firm* — Spruson & Ferguson (Hong Kong) Limited

(57) ABSTRACT

The present disclosure relates to porphyrin containing carbon quantum dots useful for bioimaging and/or phytodynamic therapy.

20 Claims, 37 Drawing Sheets

(56) References Cited

PUBLICATIONS

Sun et al.; Quantum-Sized Carbon Dots for Bright and Colorful Photoluminescence; Journal of the American Chemical Society; 2006; pp. 7756-7757; vol. 128, Issue 24; ACS Publications.

Ge et al.; Red-Emissive Carbon Dots for Fluorescent, Photoacoustic, and Thermal Theranostics in Living Mice; Advanced Materials; 2015; pp. 4169-4177; vol. 27, Issue 28; Wiley.

Ding et al.; Full-Color Light-Emitting Carbon Dots with a Surface-State-Controlled Luminescence Mechanism; ACS Nano; 2016; pp. 484-491; vol. 10, Issue 1; ACS Publications.

Ge et al.; A Graphene Quantum Dot Photodynamic Therapy Agent with High Singlet Oxygen Generation; Nature Communications; 2014; vol. 5; Article No. 4596; Nature.

Fang et al.; Easy Synthesis and Imaging Applications of Cross-Linked Green Fluorescent Hollow Carbon Nanoparticles; ACS Nano; 2012; pp. 400-409; vol. 6, Issue 1; ACS Publications.

Tang et al.; Carbon Nanodots Featuring Efficient Fret for Real-Time Monitoring of Drug Delivery and Two-Photon Imaging; Advanced Materials; 2013; pp. 6569-6574; vol. 25, Issue 45; Wiley.

Zheng et al; Integrating Oxaliplatin with Highly Luminescent Carbon Dots: an Unprecedented Theranostic Agent for Personalized Medicine; Advanced Materials; 2014; pp. 3554-3560; vol. 26, Issue 21; Wiley.

Feng et al.; Charge-Convertible Carbon Dots for Imaging-Guided Drug Delivery with Enhanced in Vivo Cancer Therapeutic Efficiency; ACS Nano; 2016; pp. 4410-4420; vol. 10, Issue 4; ACS Publications.

Wang et al.; A Two-Component Active Targeting Theranostic Agent Based on Graphene Quantum Dots; Journal of Materials Chemistry B; 2015; pp. 3583-3590; vol. 3, Issue 17; The Royal Society of Chemistry.

Beack et al.; Photodynamic Therapy of Melanoma Skin Cancer Using Carbon Dot—Chlorin e6—Hyaluronate Conjugate; Acta Biomaterialia; 2015; pp. 295-305; vol. 26; Elsevier.

Chen et al.; A Graphene Quantum Dot-Based FRET System for Nuclear-Targeted and Real-Time Monitoring of Drug Delivery; Nanoscale; 2015; pp. 15477-15486; vol. 7, Issue 37; The Royal Society of Chemistry.

Wang et al.; Carbon Nanodots Featuring Efficient FRET for Two-Photon Photodynamic Cancer Therapy with a Low Fs Laser Power Density; Biomaterials; 2014; pp. 9372-9381; vol. 35, Issue 34; Elsevier.

Huang et al.; Light-Triggered Theranostics Based on Photosensitizer-Conjugated Carbon Dots for Simultaneous Enhanced-Fluorescence Imaging and Photodynamic Therapy; Advanced Materials; 2012; pp. 5104-5110; vol. 24, Issue 37; Wiley.

Choi et al.; Highly Biocompatible Carbon Nanodots for Simultaneous Bioimaging and Targeted Photodynamic Therapy in Vitro and in Vivo; Advanced Functional Materials; 2014; pp. 5781-5789; vol. 24, Issue 37; Wiley.

Song et al.; Anti-HIF-1α Antibody-Conjugated Pluronic Triblock Copolymers Encapsulated with Paclitaxel for Tumor Targeting Therapy; Biomaterials; 2010; pp. 2302-2312; vol. 31, Issue 8; Elsevier.

William JR et al.; Molecular Targets for Cancer Chemoprevention; Nature Reviews Drug Discovery; 2009; pp. 213-225; vol. 8; Nature.

Farokhzad et al.; Targeted Nanoparticle-Aptamer Bioconjugates for Cancer Chemotherapy in Vivo; Proceedings of the National Academy of Sciences of the United States of America; 2006; pp. 6315-6320; vol. 103, Issue 16; United States National Academy of Sciences.

Baselga; The EGFR as a Target for Anticancer Therapy—Focus on Cetuximab; European Journal of Cancer; 2001; pp. 16-22; vol. 37, Supplement 4; Elsevier.

Gao et al.; Targeted Imaging of EGFR Overexpressed Cancer Cells by Brightly Fluorescent Nanoparticles Conjugated with Cetuximab; Nanoscale; 2016; pp. 15027-15032; vol. 8, Issue 32; The Royal Society of Chemistry.

Dong et al.; Polyamine-Functionalized Carbon Quantum Dots for Chemical Sensing; Carbon; 2012; pp. 2810-2815; vol. 50, Issue 8; Elsevier.

Hu et al.; Tunable Photoluminescence across the Entire Visible Spectrum from Carbon Dots Excited by White Light; Angewandte Chemie International Edition; 2015; pp. 2970-2974; vol. 54, Issue 10; Wiley.

Qu et al.; A Biocompatible Fluorescent Ink Based on Water-Soluble Luminescent Carbon Nanodots; Angewandte Chemie International Edition; 2012; pp. 12215-12218; vol. 51, Issue 49; Wiley.

Dong et al.; Carbon-Based Dots Co-Doped with Nitrogen and Sulfur for High Quantum Yield and Excitation-Independent Emission; Angewandte Chemie International Edition; pp. 7800-7804; 2013; vol. 52, Issue 30; Wiley.

Zhao et al.; Green Synthesis of Bifunctional Fluorescent Carbon Dots from Garlic for Cellular Imaging and Free Radical Scavenging; ACS Applied Materials & Interfaces; 2015; pp. 17054-17060; vol. 7, Issue 31; ACS Publications.

Zhang et al.; Synthesis and Magnetic Properties of Zr Doped ZnO Nanoparticles; Nanoscale Research Letters; 2011; pp. 587-594; vol. 6; Springer.

Sun et al.; Host-Guest Carbon Dots for Enhanced Optical Properties and Beyond; Scientific Reports; 2015; vol. 5; Article No. 12354; Nature.

Zhu et al.; Highly Photoluminescent Carbon Dots for Multicolor Patterning, Sensors, and Bioimaging; Angewandte Chemie International Edition; 2013; pp. 3953-3957; vol. 52, Issue 14; Wiley.

Baskaran et al.; Carbon Nanotubes with Covalently Linked Porphyrin Antennae: Photoinduced Electron Transfer; Journal of the American Chemical Society; 2005; pp. 6916-6917; vol. 127, Issue 19; ACS Publications.

Bourré et al.; Indirect detection of photosensitizer ex vivo; Journal of Photochemistry and Photobiology B: Biology; 2002; pp. 23-31; vol. 67, Issue 1; Elsevier.

Zhang et al.; A Porphyrin Photosensitized Metal—Organic Framework for Cancer Cell Apoptosis and Caspase Responsive Theranostics; Chemical Communications; 2015; pp. 10831-10834; vol. 51, Issue 54; The Royal Society of Chemistry.

Marydasan et al.; Optimization of Triplet Excited State and Singlet Oxygen Quantum Yields of Picolylamine—Porphyrin Conjugates through Zinc Insertion; The Journal of Physical Chemistry B; 2013; pp. 13515-13522; vol. 117, Issue 43; ACS Publications.

Meng et al.; A Self-Assembled M8L6 Cubic Cage that Selectively Encapsulates Large Aromatic Guests; Angewandte Chemie International Edition; 2011; pp. 3479-3483; vol. 50, Issue 15; Wiley.

* cited by examiner

CONJUGATED PORPHYRIN CARBON QUANTUM DOTS FOR TARGETED PHOTODYNAMIC THERAPY

CROSS-REFERENCE TO RELATED APPLICATIONS

This application claims priority from U.S. Provisional Patent Application Ser. No. 62/419,454 filed on Nov. 8, 2016, the disclosure of which is hereby incorporated by reference.

FIELD OF THE INVENTION

The present disclosure relates to biocompatible porphyrin carbon quantum dots conjugated to a targeting agent. More particularly, the present disclosure relates to red emissive cetuximab-conjugated porphyrin carbon quantum dots (C225-PCQDs) that precisely target non-small lung cancer cells and lead to remarkable photodynamic therapy (PDT), demonstrating its high potential for targeted imaging and PDT of non-small lung cancer.

BACKGROUND OF THE INVENTION

Carbon nanomaterials have garnered much interest due to their potential applications in bioimaging, photocatalysis, and light-emitting devices. Since 2006, carbon quantum dots ("CQDs") have been utilized as fluorescent agents for biomedical applications, especially for in vitro and in vivo fluorescence bioimaging. In addition to their use as fluorescence imaging agents, CQDs have also found use as drug delivery agents by conjugating the CQD with active therapeutic drugs or biomolecules, such as doxorubicin (DOX), platinum-based drugs, aptamer, protein and so on, through surface functionalization for simultaneous imaging and therapeutic applications. For example, Huang et al. designed a novel theranostic platform based on carbon quantum dots conjugated with a photosensitizer. The conjugation of phytochlorin ("Ce6") with a CQD can overcome some of the disadvantages of unmodified phytochlorin, such as prolonged cutaneous photosensitivity, poor water solubility and inadequate selectivity. The prepared CQD-Ce6 displayed enhanced photosensitizer fluorescence detection and remarkable photodynamic efficacy upon irradiation, which could act as a good candidate for simultaneous enhanced photosensitizer fluorescence detection (PFD) and photodynamic therapy (PDT) of gastric cancer tumor. Recently, Choi et al. developed a similar theranostic platform based on folic acid (FA) conjugated carbon dots loaded with zinc(II)-phthalocyanine to realize targeted delivery and photodynamic therapy.

However, the preparation of CQD-based drug delivery systems involves complex, multistep and time-consuming reactions, and inconvenient post-synthetic treatments. Thus, developing a simple and convenient way for the preparation of porphyrin-based carbon quantum dots remains highly desirable. In addition, the active targeted drug delivery and release technology has become a major area of research, as it can reduce systemic exposure to the drug and thus decrease the drug's side effects. These advantages are particularly important in the administration of therapeutics with harmful side effects, such as anti-cancer agents. Therefore, there is a need to develop new targeted delivery methods useful in the targeted treatment of diseases, such as cancer.

SUMMARY OF THE INVENTION

Accordingly, it is an objective of the present disclosure to provide biocompatible porphyrin carbon quantum dots (such as C225-PCQDs) that are capable of precisely targeting a desired cellular target. In the examples below, a red emissive cetuximab-conjugated PCQD is prepared and its ability to target non-small lung cancer cells and its use in photodynamic therapy (PDT) is demonstrated. The results show that C225-PCQDs can selectively accumulate in cancer cells that over-express EGFR and be used as an effective platform for simultaneous imaging and targeted PDT of cancer.

In a first aspect of the present disclosure, provided herein is a nanoparticle comprising a carbon matrix and one or more moieties present on the surface of the carbon matrix, wherein the one or more moieties is selected from the group consisting of $-CO_2H$ and $-C(=O)NH(CH_2CH_2O)_n CH_2CH_2NHR$, wherein n is a whole number selected from 3-100 and R is a hydrogen or a targeting group; and the carbon matrix comprises a compound of Formula I:

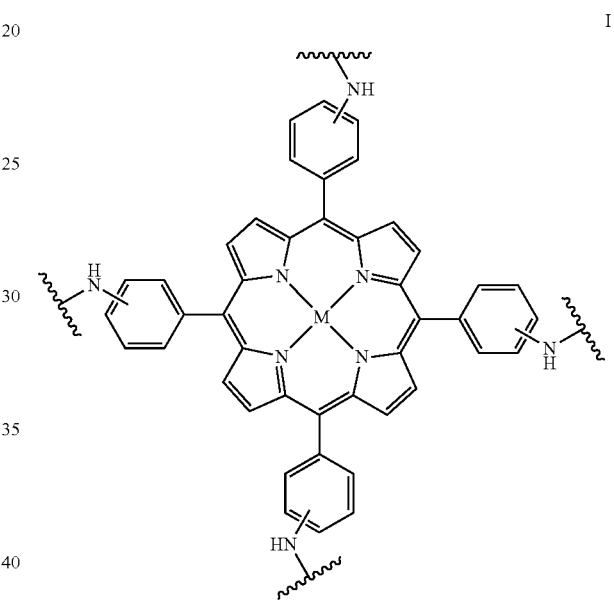

wherein, M is a metal selected from the group consisting of Co, Ni, Mn, Zn, Pt, and Pd; or M represents two hydrogen, each of which is covalently bound to a nitrogen; and

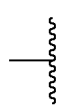

represents a covalent nitrogen-carbon bond between the compound of Formula I and the carbon matrix.

In a first embodiment of the first aspect of the present disclosure there is provided a nanoparticle, wherein n is a whole number selected from 3-40.

In a second embodiment of the first aspect of the present disclosure there is provided a nanoparticle, wherein the nanoparticle has an average diameter of about 3 to about 3.5 nm.

In a third embodiment of the first aspect of the present disclosure there is provided a nanoparticle, wherein the carbon matrix comprises graphitic carbon.

In a fourth embodiment of the first aspect of the present disclosure there is provided a nanoparticle, wherein the targeting group is selected from the group consisting of an antibody, an antibody fragment, a peptide, an aptamer, and a small molecule.

In a fifth embodiment of the first aspect of the present disclosure there is provided a nanoparticle, wherein the targeting group is selected from the group consisting of an antibody, an antibody fragment, a peptide, an aptamer, and a small molecule and the antibody is cetuximab or panitumumab; the peptide is a cyclic RGD peptide; and the aptamer is anti-nucleolin aptamer AS1411.

In a sixth embodiment of the first aspect of the present disclosure there is provided a nanoparticle, wherein the nanoparticle has an average diameter of about 3 to about 3.5 nm; n is whole number selected from 3-40; the carbon matrix comprises graphitic carbon; M is Zn; or M represents two hydrogen, each of which is covalently bound to a nitrogen; and R is cetuximab.

In a second aspect of the present disclosure provided herein is a method for treating non-small cell lung cancer in a patient in need thereof, comprising the step of administering a therapeutically effective amount of the nanoparticle of the first aspect.

In a third aspect of the present disclosure provided herein is a method for imaging a cell that overexpresses epidermal growth factor receptor (EGFR), comprising the step of contacting the cell with the nanoparticle of the sixth embodiment of the first aspect and detecting the fluorescence of the nanoparticle of the sixth embodiment of the first aspect.

In a fourth aspect of the present disclosure provided herein is a method of synthesizing the nanoparticle of the first aspect, comprising the steps of:
a) contacting an organic acid selected from the group consisting of aspartic acid, citric acid, ethylenediaminetetraacetic acid (EDTA), glutamic acid, and tartaric acid with a compound of Formula II:

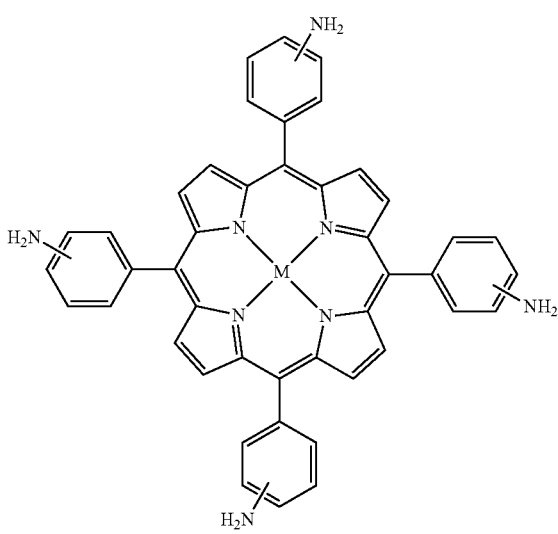

wherein, M is a metal selected from the group consisting of Co, Ni, Mn, Zn, Pt, and Pd; or M represents two hydrogen, each of which is covalently bound to a nitrogen; thereby forming a polymerized polyamide;
b) subjecting the polymerized polyamide to hydrothermal carbonization thereby forming an unfunctionalized nanoparticle comprising a carbon matrix and one or more —$CO_2H$ present on the surface of the carbon matrix; and the carbon matrix comprises a compound of Formula I:

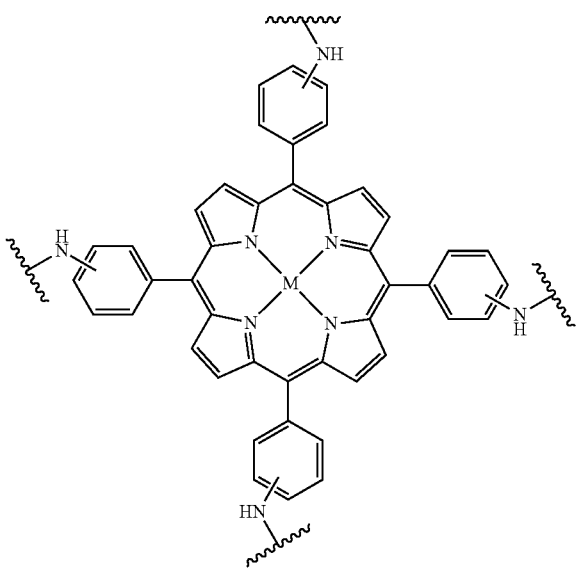

wherein, M is a metal selected from the group consisting of Co, Ni, Mn, Zn, Pt, and Pd; or M represents two hydrogen, each of which is covalently bound to a nitrogen; and

represents a covalent nitrogen-carbon bond between the compound of Formula I and the carbon matrix;
c) contacting the unfunctionalized nanoparticle with $NH_2(CH_2CH_2O)_nCH_2CH_2NH_2$, wherein n is a whole number selected from 3-100, under conditions for forming an amide bond, thereby forming an amine terminated nanoparticle; and
d) optionally contacting the amine terminated nanoparticle with a targeting group comprising an activated carbonyl thereby forming the nanoparticle of the first aspect.

In a first embodiment of the fourth aspect of the present disclosure provided herein is a method, wherein the step of contacting the compound of Formula II and the organic acid, the compound of Formula II and organic acid are present in a mass to mass ratio of about 1:10 to about 1:15 of the compound of Formula II to the organic acid.

In a second embodiment of the fourth aspect of the present disclosure provided herein is a method, wherein the organic acid is citric acid.

In a third embodiment of the fourth aspect of the present disclosure provided herein is a method, wherein n is a whole number selected from 3-40.

In a fourth embodiment of the fourth aspect of the present disclosure provided herein is a method, wherein n is a whole number selected from 3-40 and the step of contacting the contacting the unfunctionalized nanoparticle with $NH_2$ $(CH_2CH_2O)_nCH_2CH_2NH_2$, the unfunctionalized nanoparticle and $NH_2(CH_2CH_2O)_nCH_2CH_2NH_2$ are present in a mass to mass ratio of about 1:10 to about 1:15 the unfunctionalized nanoparticle to the $NH_2(CH_2CH_2O)CH_2CH_2O)_nCH_2CH_2NH_2$.

In a fifth aspect of the present disclosure provided herein is a nanoparticle made according to the method of the fourth embodiment of the fourth aspect of the present disclosure.

In a fifth embodiment of the fourth aspect of the present disclosure provided herein is a method, wherein the targeting group is selected from the group consisting of an antibody, an antibody fragment, a peptide, an aptamer, and a small molecule.

In a sixth embodiment of the fourth aspect of the present disclosure provided herein is a method, further comprising the step of purifying the unfunctionalized nanoparticle by dialysis.

In a seventh embodiment of the fourth aspect of the present disclosure provided herein is a method, wherein the hydrothermal carbonization is conducted at a temperature between about 160° C. to about 240° C.

In an eighth embodiment of the fourth aspect of the present disclosure provided herein is a method, wherein the nanoparticle has an average diameter of about 3 to about 3.5 nm; n is whole number selected from 3-40; the carbon matrix comprises graphitic carbon; M is Zn; or M represents two hydrogen, each of which is covalently bound to a nitrogen; and the targeting group comprising an activated carbonyl is cetuximab comprising an activated carbonyl.

In a sixth aspect of the present disclosure provided herein is a nanoparticle made according to the method of the eighth embodiment of the fourth aspect of the present disclosure.

If desired, the different functions discussed herein may be performed in a different order and/or concurrently with each other. Furthermore, if desired, one or more of the above-described functions may be optional or may be combined.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extent. All publications recited herein are hereby incorporated by reference in their entirety.

Citation or identification of any reference in this section or any other section of this document shall not be construed as an admission that such reference is available as prior art for the present application.

BRIEF DESCRIPTION OF DRAWINGS

The above and other objects and features of the present invention will become apparent from the following description of the invention, when taken in conjunction with the accompanying drawings, in which.

DETAILED DESCRIPTION OF THE INVENTION

Figure 1A:
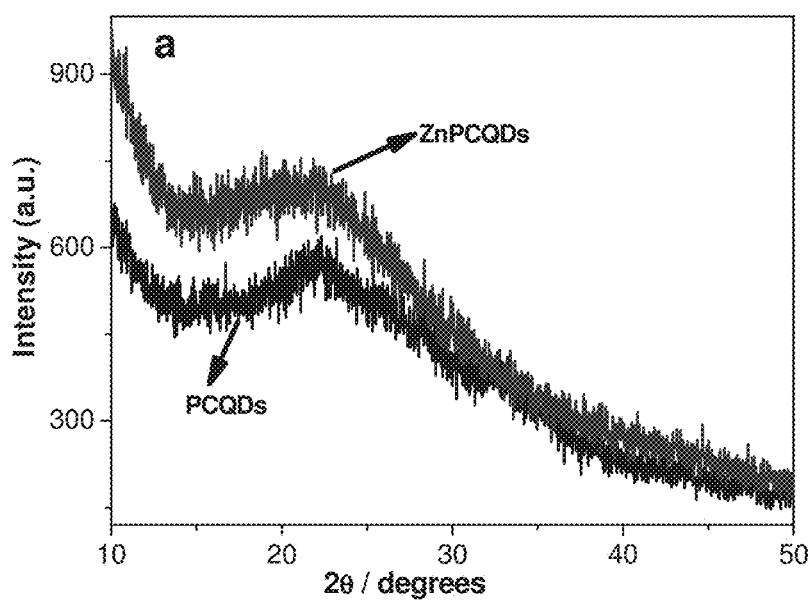
FIG. 1A shows an x-ray diffraction (XRD) pattern of the PCQDs and ZnPCQDs.

The present disclosure is not to be limited in scope by any of the specific embodiments described herein. The following embodiments are presented for exemplification only.

Provided herein are porphyrin carbon quantum dots (e.g., (Zn)PCQDs) that can be prepared in a straight forward one-pot hydrothermal carbonization process. The PCQD nanoparticles are well characterized and the porphyrin, which has high thermal stability, is substantially encapsulated in the core of carbon quantum dots without significant, if any, decomposition of the porphyrin ring.

Tetraamino-porphyrins (TAP) useful for preparing the nanoparticles described herein can be represented by the compound of Formula II:

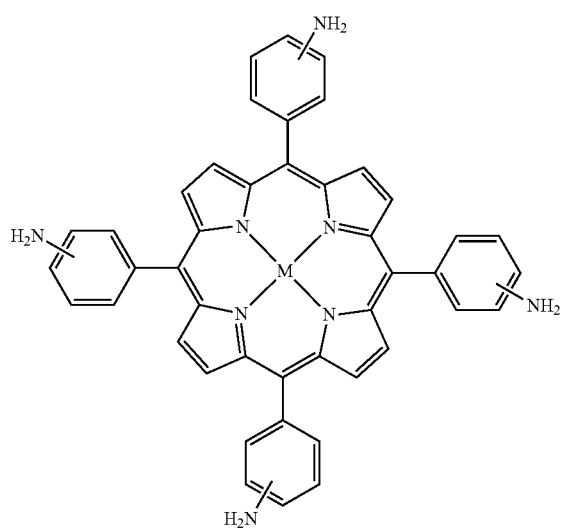

II wherein, each of the amines can be independently covalently bonded to the ortho, meta, or para position of the phenyl ring to which they are attached and M can be any metal capable of binding to the porphyrin. In certain embodiments, the TAP is the compound of Formula II, wherein M is a transition metal. In certain embodiments, the TAP is the compound of Formula II, wherein M is selected from the group consisting of Co, Ni, Mn, Zn, Pt, and Pd.

In other embodiments, the TAP is the compound of Formula II, wherein M represents two hydrogen, each of which is covalently bound to a nitrogen and can be represented by the compound of Formula III:

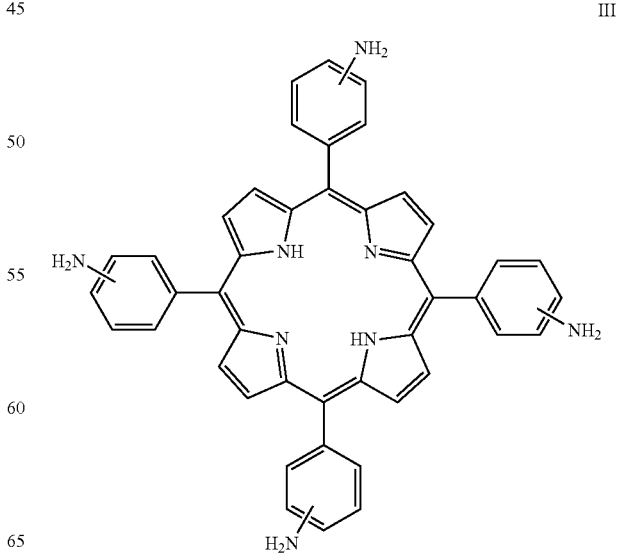

III wherein, each of the amines can be independently covalently bonded to the ortho, meta, or para position of the phenyl ring to which they are attached.

In certain embodiments, the TAP can be represented by a compound of Formula IV:

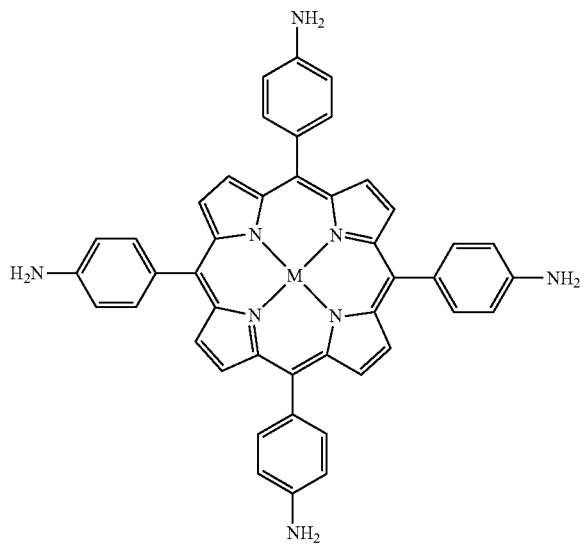

IV wherein, M is Zn; or M represents two hydrogen, each of which is covalently bound to a nitrogen.

In certain embodiments, the TAP is a conjugate acid of the compound of Formula II-IV. The conjugate acid can be a salt of a compound of Formula II-IV with an acid, such as HCl, HBr, $H_2SO_4$, $HSO_4-$, $HNO_3$, $H_3PO_4$, and the like.

The compound of Formula II-IV, or its conjugate acid is reacted with an organic acid thereby forming a polymerized polyamide. Organic acids suitable for preparing the polymerized polyamide can contain two or more carboxylic acids. In certain embodiments, the organic acid is selected from the group consisting of citric acid, EDTA, tartaric acid, glutamic acid, aspartic acid, and any combination thereof. In certain embodiments the organic acid can be $HO_2C(CH2)_mCO_2H$, wherein m is 2-10.

The organic acid and the compound of Formula II-IV can be reacted in a mass ratio of about 1:10 to about 1:15 of the compound of Formula II-IV to the organic acid.

In certain embodiments, the polymerized amide is prepared from polymerizing the compound of Formula II-IV and citric acid thereby forming a polymerized amide comprising a compound of Formula V:

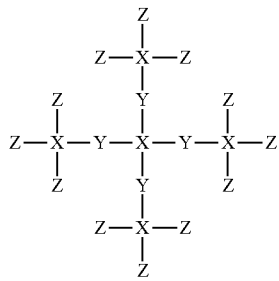

V wherein X represents the compound of Formula I:

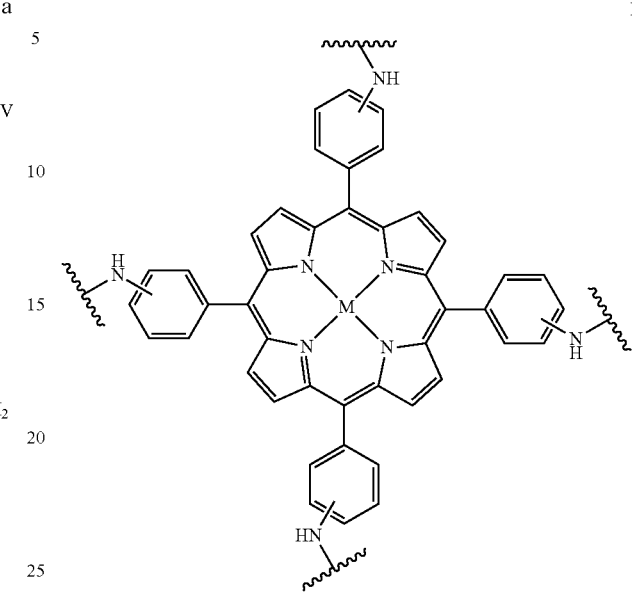

I

Y represents a compound of Formula VI:

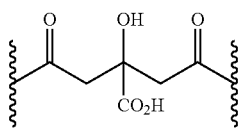

wherein, each carboxyl group is covalently bonded to an amine group attached to the compound of Formula I; and each instance of Z is independently selected from the group consisting of hydrogen, a compound of Formula VII:

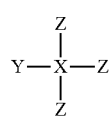

VII and a compound of Formula VIII

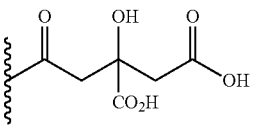

VIII wherein each carboxyl group is covalently bonded to an amine group attached to the compound of Formula I.

The polymerized amide is then subjected to hydrothermal carbonization treatment. Hydrothermal carbonization refers to a method in which a carbon containing compound or mixture is heated at an elevated temperature in water or an alcohol (such as ethanol) to yield a carbon matrix comprising graphitic carbon. Hydrothermal carbonization can be conducted in an enclosed vessel, such as a pressure reactor, or at atmospheric pressure.

The hydrothermal carbonization can be conducted at a temperature that converts substantially all of the organic acid to a carbon matrix comprising graphitic carbon. In certain embodiments, the hydrothermal carbonization is conducted at a temperature that converts substantially all of the organic acid to a carbon matrix comprising graphitic carbon and does not substantially decompose the porphyrin. The selection of the hydrothermal carbonization temperature can be determined based on the properties of the organic acid and is well within the skill of a person of ordinary skill in the art. The hydrothermal carbonization can be conducted at a temperature of about 160° C. to about 240° C. In certain embodiments, the hydrothermal carbonization treatment is conducted at about 170° C. to about 230° C.; about 180° C. to about 230° C.; about 180° C. to about 220° C.; about 190° C. to about 220° C.; about 190° C. to about 210° C.; or about 195° C. to about 205° C.

The polymerized amide can be subjected to hydrothermal carbonization until substantially all of the organic acid is converted to a carbon matrix comprising graphitic carbon. In certain embodiments, the reaction is halted once all of the organic acid has been consumed and/or when the porphyrin begins to decompose. The hydrothermal carbonization reaction time can be determined based on the type of organic acid and compound of Formula II-IV used and concentration of the components. The polymerized amide can subjected to hydrothermal carbonization for about 1 to 5 hours. In certain embodiments, the polymerized amide is subjected to hydrothermal carbonization for about 2 to about 5 hours, or about 2 to about 4 hours.

Treatment of the polymerized amide to hydrothermal carbonization yields an unfunctionalized nanoparticle, which can optionally be purified. In certain embodiments, the unfunctionalized nanoparticle is purified by dialysis.

In order to functionalize the surface of the unfunctionalized nanoparticle, the surface of the unfunctionalized nanoparticle can be conjugated to a linker, such as a poly (ethylene glycol)diamine, to yield an amine terminated nanoparticle with modified physical chemical properties (such as improved water solubility and absorption) and a functional group (such as a terminal amine) that can be used to covalently bond a targeting group. A targeting group can then be attached to the amine terminated nanoparticle to produce a compound of Formula I. In the examples bellows, the amine terminated nanoparticle is conjugated with cetuximab, resulting in a novel cetuximab-conjugated porphyrin carbon quantum dot (C225-PCQDs). The C225-PCQDs can precisely target non-small lung cancer cells with overexpression of EGFR (HCC827 cells) and be used in photodynamic therapy (PDT) on non-small lung cancer cells, demonstrating its high potential for targeted imaging and PDT of non-small lung cancer.

The unfunctionalized nanoparticle has one or more hydroxyls and/or carboxylic acids on its surface, which can be covalently reacted with a linker to facilitate conjugation of the unfunctionalized nanoparticle with the targeting group. Any linker known in the art that is capable of reacting with a hydroxyl and/or carboxylic acid can be utilized. In certain embodiments, the linker is a diamine or an aminoalcohol. In certain embodiments, the linker can be represented by $NH_2(CH_2CH_2O)_nCH_2CH_2NH_2$ or $HO(CH_2CH_2O)_nCH_2CH_2NH_2$, wherein n is a whole number selected from 3-100. In certain embodiments, n is between about 3 to about 90, about 3 to about 80, about 3 to about 70, about 3 to about 60, about 3 to about 50, about 3 to about 40, about 5 to about 40, about 10 to about 40, or about 20 to about 50.

The linker can be reacted with the unfunctionalized nanoparticle using any method known to those of skill in the art. In the examples below, the diamine linker is reacted with the unfunctionalized nanoparticle using a condensation reaction thereby yielding an amine terminated nanoparticle.

The amine terminated nanoparticle can be used to conjugate to a targeting agent. The targeting agent can be an antibody, an antibody fragment (such as Fab, Fab', F(ab')$_2$, Fv), single chain (ScFv)) a peptide, an aptamer, or a small molecule that is capable of selectively binding to a target of interest, such as a carbohydrate, polynucleotide, lipid, polypeptide, etc.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule.

The antibody can be an antibody known in the art. In certain embodiments, the antibody is useful for treating cancer, such as cetuximab trastuzumab, bevacizumab, panitumumab, rituximab, alemtuzumab, ofatumumab, gemtuzumab ozogamicin, brentuximab vedotin, The peptide can be a cyclic RGD peptide. The aptamer can be anti-nucleolin aptamer AS1411.

The targeting agent can be conjugated to the amine terminated nanoparticle using a carbonyl activating agent. Any carbonyl activating agent known in the art can be used. In certain embodiments, the carbonyl activating agent is selected from the group consisting of chlorotriazine, cyclohexylcarbodiimide (DCC), 1,1-carbonyldiimidazole (CDI), 1-Ethyl-3-(3-dimethylaminopropyl)carbodiimide (EDI), benzotriazol-1-yloxy) tripyrrolidinophosphonium hexafluorophosphate (PyBOP), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), and the like, which can be reacted with the targeting agent thereby yielding the targeting group comprising an activated carbonyl. The carbonyl activating agent can optionally be used together with a catalytic amount of 4-dimethylaminopyridine (DMAP) N-hydroxysuccinimide (NHS), or N-hydroxy benzotriazole.

A biocompatible red emissive cetuximab-conjugated porphyrin carbon quantum dot (C225-PCQD) was developed. Cetuximab was chosen as a representative targeting group as it is able to recognize and target, with high binding affinity, the epidermal growth factor receptor (EGFR), a transmembrane receptor tyrosine kinase highly expressed on many human malignancies, such as head and neck, colorectal, non-small cell lung, and gastric cancers. To evaluate the targeting ability, C225-PCQDs was used to bioimage HCC827 cells (which are known to over-express of EGFR) and H23 cells (which are known to have low expression of EGFR), and its subcellular localization was evaluated by confocal laser scanning microscope. The laser-induced PDT effect of C225-PCQDs on HCC827 cells and HLF cells was studied and evaluated by cell counting kit-8 (CCK-8) cell proliferation cytotoxicity assay.

Synthesis of PCQDs and C225-PCQDs.

Figure 16:
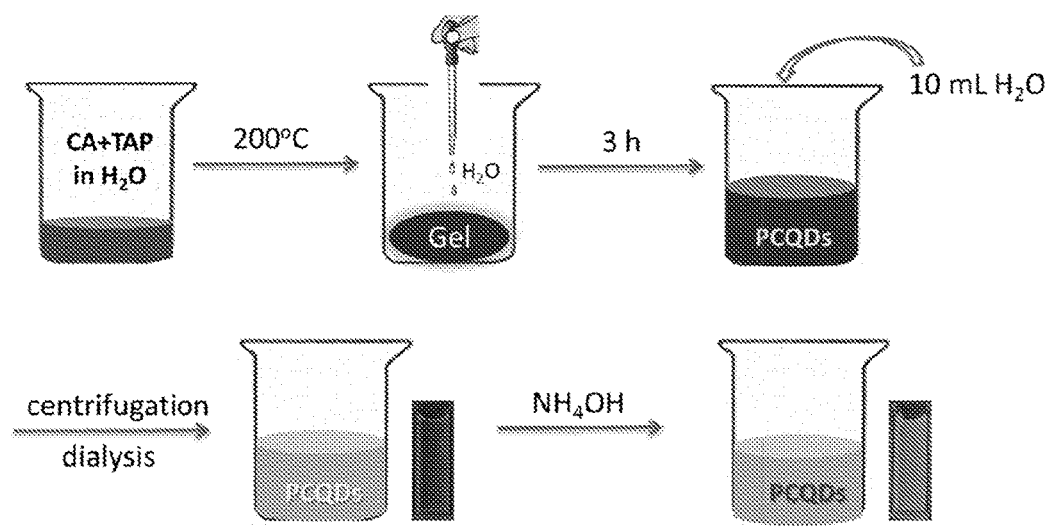
FIG. 16 shows a schematic illustration of one-pot synthesis of PCQDs. The inset shows the photograph of PCQDs in aqueous solution under UV light (365 nm).
Figure 17:
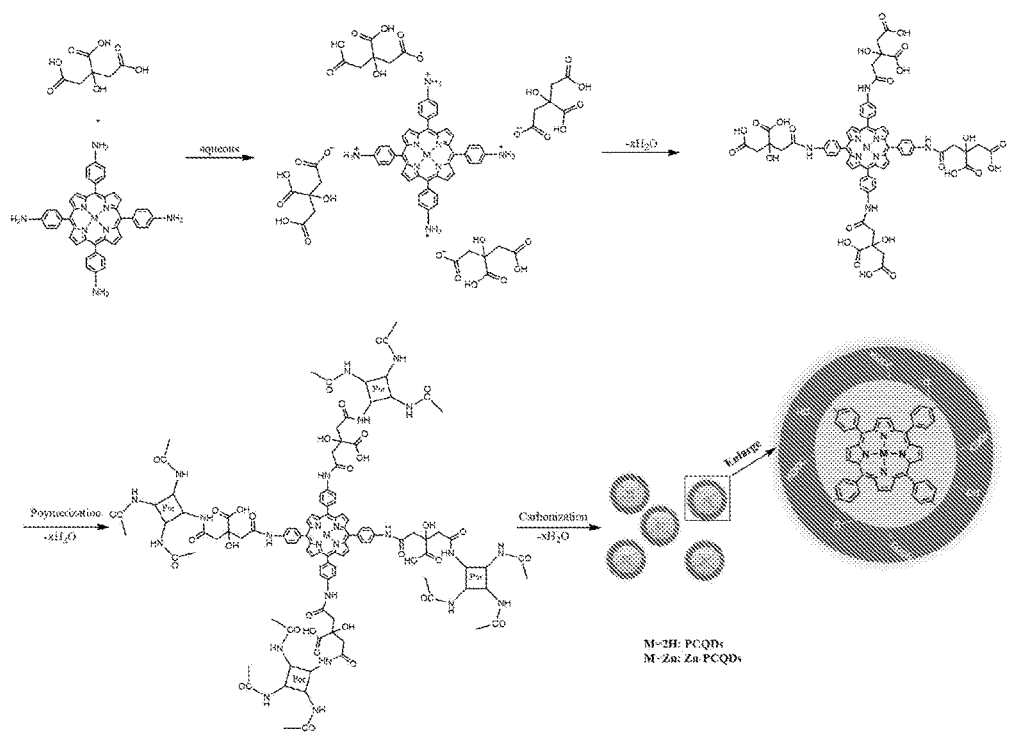
FIG. 17 shows the proposed formation pathway of PCQDs and ZnPCQDs.
Figure 18:
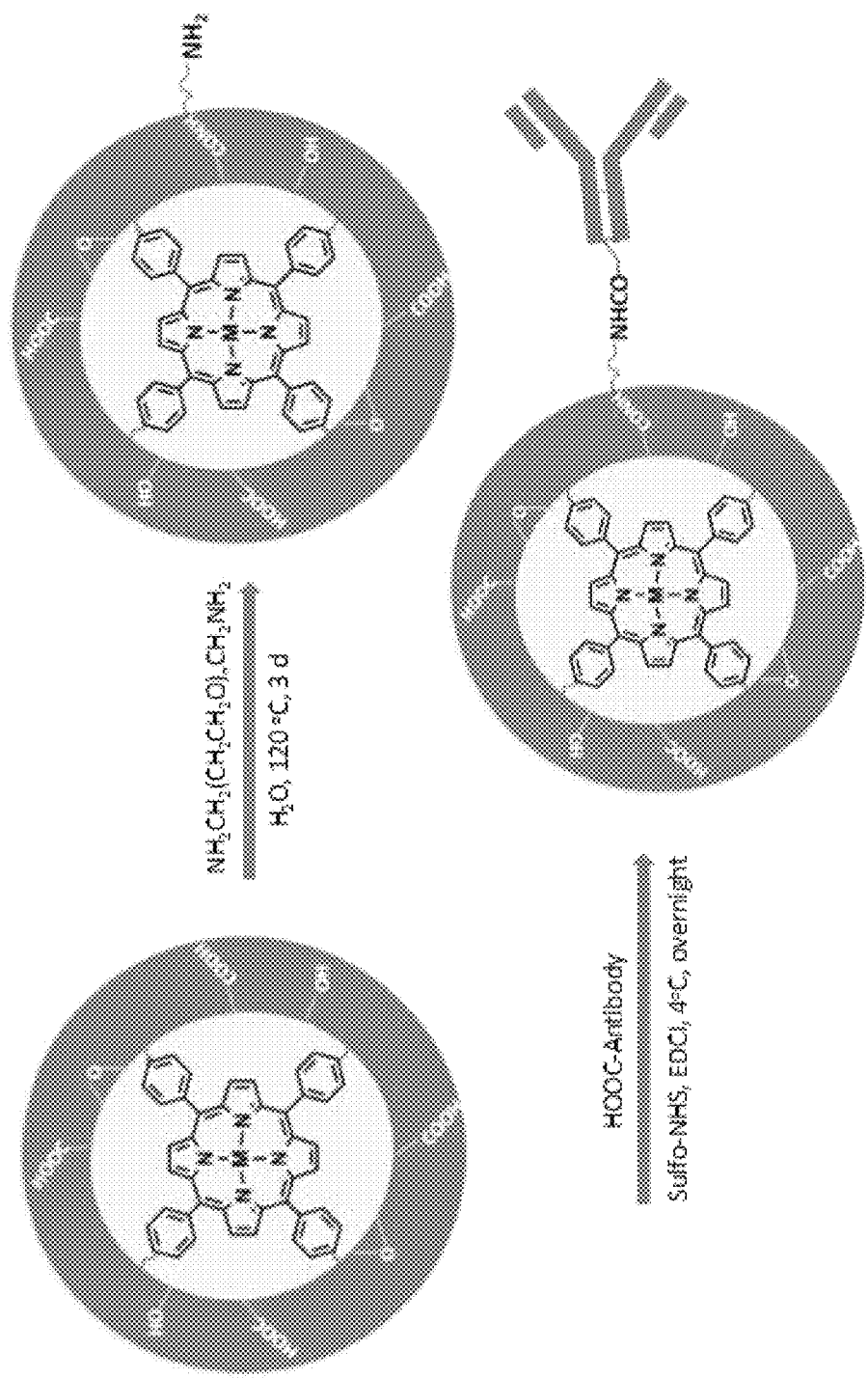
FIG. 18 shows the synthetic procedure of C225-PCQDs.

As shown in FIG. 16, the PCQDs and ZnPCQDs were prepared by a one-step pyrolysis of citric acid (CA) in the presence of 5,10,15,20-tetrakis(4-aminophenyl)porphyrin (TAP) or its complex Zn(II)TAP. Specifically, 0.1 g TAP and 1.0 g CA were dissolved in 20 mL deionized (DI) water, and then sonicated for 10 min at room temperature. The uniform solution was heated to 200° C. with a heating mantle. When the gel was formed, 2 mL of DI water was added to prevent it from scorching and heating was continued. The same procedure was repeated for 3 hours. After the reaction, the obtained PCQDs was cooled to room temperature and dispersed in 10 mL DI water. The resulting dark brown solution was centrifuged at 15,000 rpm for 30 min to remove weight precipitate and agglomerated particles and then was dialyzed against DI water for three days, yielding a green aqueous solution of PCQDs. The solid product was collected after freeze-drying and could be dissolved again in water for further characterization and use. The ZnPCQDs were prepared with the same method with Zn(II)TAP as passivation agent and ethanol as solvent. The assumed process of formation of PCQDs and ZnPCQDs was shown in FIG. 17. In this system, CA was used as carbon source, while TAP or Zn(II)TAP as passivation agents. As shown in FIG. 17, with the reaction progresses from low to high temperature, the polymer-like CQDs are changed into carbogenic CQDs. For the preparation of PCQDs and ZnPCQDs, the appropriate temperature was set between 180° C. and 220° C., as it advantageously allows complete carbonization of citric acid without substantial, if any, degradation of the porphyrin or its metal complex. When the temperature exceeds 220° C., the porphyrin in the core layer of carbon quantum dots can gradually decompose. The amount of encapsulated porphyrin and zinc porphyrin, calculated from the standard curve of the UV-Vis absorbance of TAP and Zn(II)TAP, was about 232 g and 306 g per milligram of PCQDs and ZnPCQDs, respectively. Subsequently, the surface of PCQDs was functionalized with PEG diamine (PEG1500N) to afford the PEG-coated carbon quantum dots ($NH_2$-PCQDs) with terminated amine groups. The cetuximab was then covalently bonded to $NH_2$-PCQDs using a modified EDC-NHS reaction, yielding the cetuximab-conjugated porphyrin carbon quantum dots (C225-PCQDs), as shown in FIG. 18.

Figure 19:
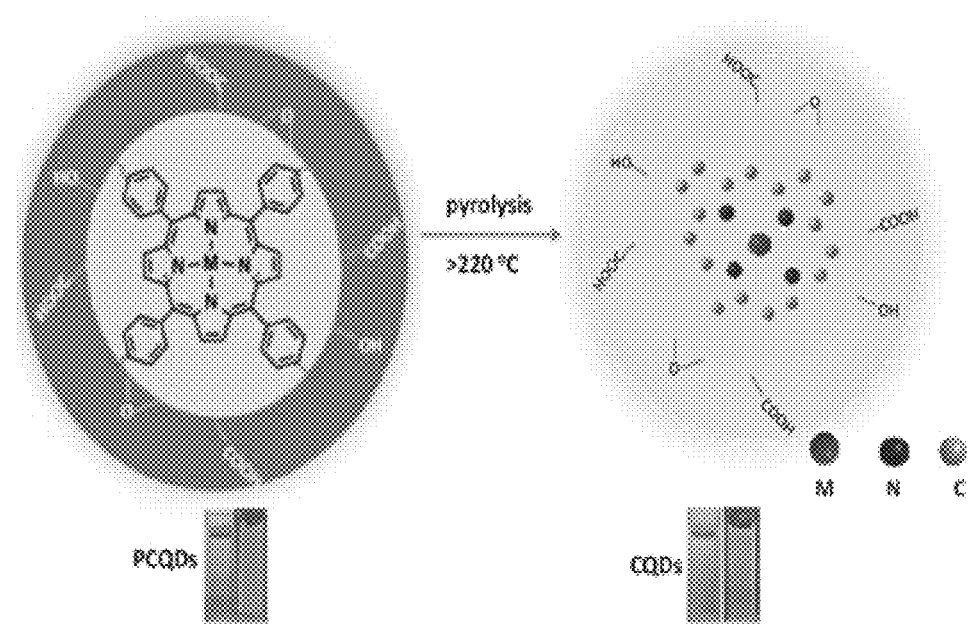
FIG. 19 shows the decomposition of porphyrin in the core of PCQDs to CQDs.

The hydrothermal temperature is an important factor for the preparation of porphyrin carbon quantum dots (PCQDs). With the reaction progresses from low temperature to high temperature, the polymer-like CQDs are changed into carbogenic CQDs. For the preparation of PCQDs, the hydrothermal carbonization treatment can be conducted at a temperature of about 180° C. to about 220° C., as it advantageously allows complete carbonization of CA without substantial, if any, degeneration of tetraamino-porphyrin (TAP). When temperature is higher than 220° C., the porphyrin in the core layer of carbon quantum dots can gradually decompose and the PCQDs will change to carbon quantum dots (CQDs) that do not comprise a compound of Formula I, as shown in FIG. 19.

Structural and Morphological Characterization.

The structures of as-prepared materials were unambiguously demonstrated by X-ray diffraction (XRD), Zeta potential measurement, and X-ray photoelectron spectroscopy (XPS). As shown in FIG. 1A, the typical XRD profiles for PCQDs and ZnPCQDs both show the 2θ diffraction peaks centered at 22° (0.34 nm), which is attributed to the highly disordered carbon atoms, similar to the graphite (002) lattice spacing.

Figure 1B:
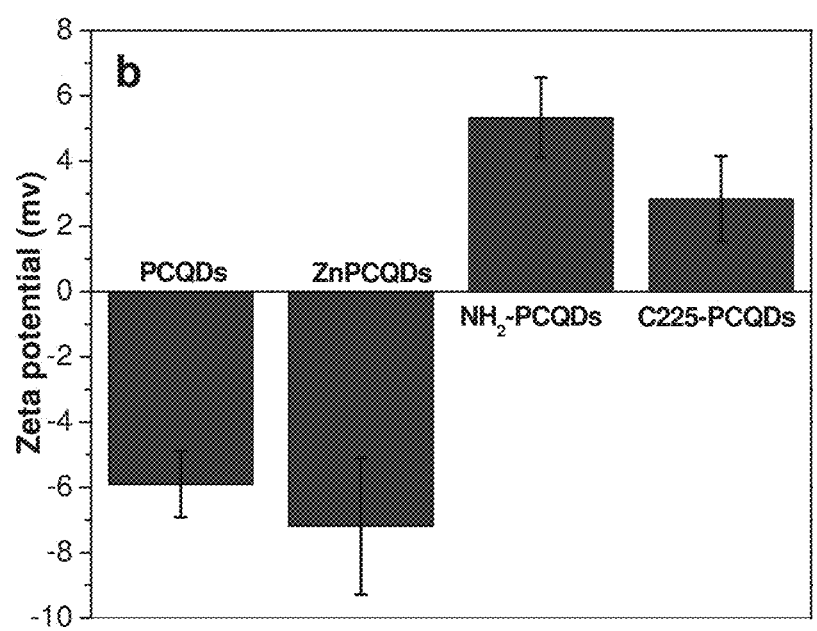
FIG. 1B shows zeta potential of PCQDs, ZnPCQDs, $NH_2$-PCQDs and C225-PCQDs.

Zeta potential is widely used as the indicator of the magnitude of the charge and the stability of nanomaterials. The zeta potential of PCQDs was recorded as −5.90 mV at pH 7.0 (FIG. 1B), due to the existence of —OH/—COOH groups on the surface of porphyrin carbon quantum dots. When Zn(II)TAP is used as passivation agent, the zeta potential changed to −7.19 mV, owing to the absence of protonation inside of ZnPCQDs. The two materials both bear negative charges, which may be responsible for the high water dispersity and solubility of porphyrin carbon quantum dots. After functionalization of PCQDs with PEG diamine, the zeta potential of $NH_2$-PCQDs becomes 5.33 mV, indicating the loss of the carboxylic acid groups upon surface functionalization. The zeta potential of C225-PCQDs further decreased to 2.84 mV when conjugated with cetuximab.

Figure 2A:
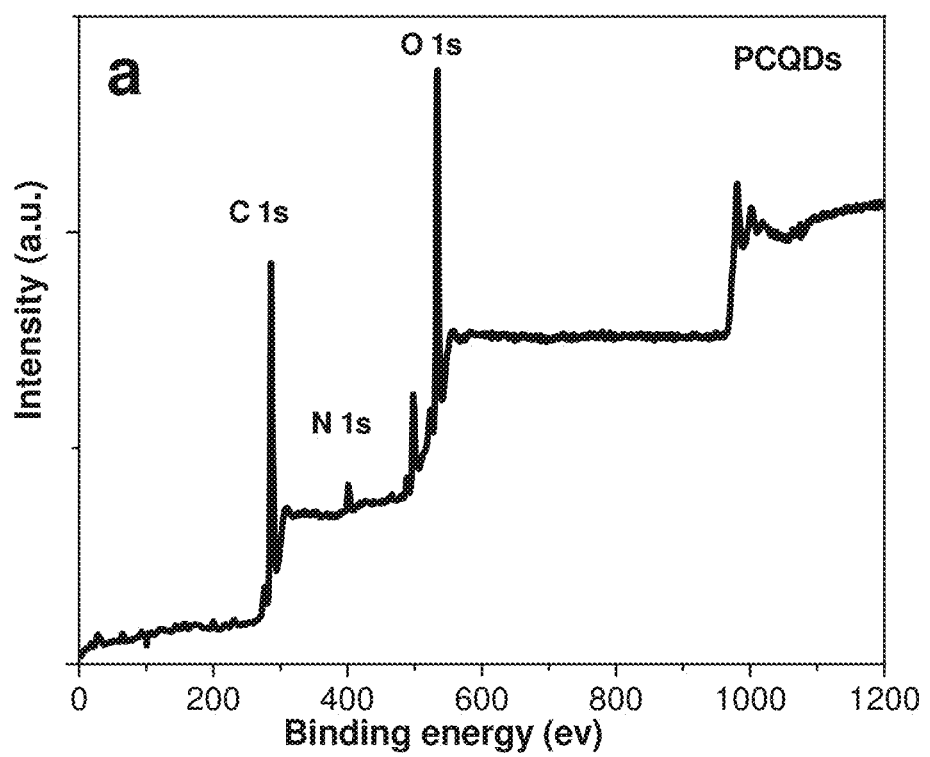
FIG. 2A shows an X-ray photoelectron spectroscopy (XPS) survey spectra of PCQDs.
Figure 2B:
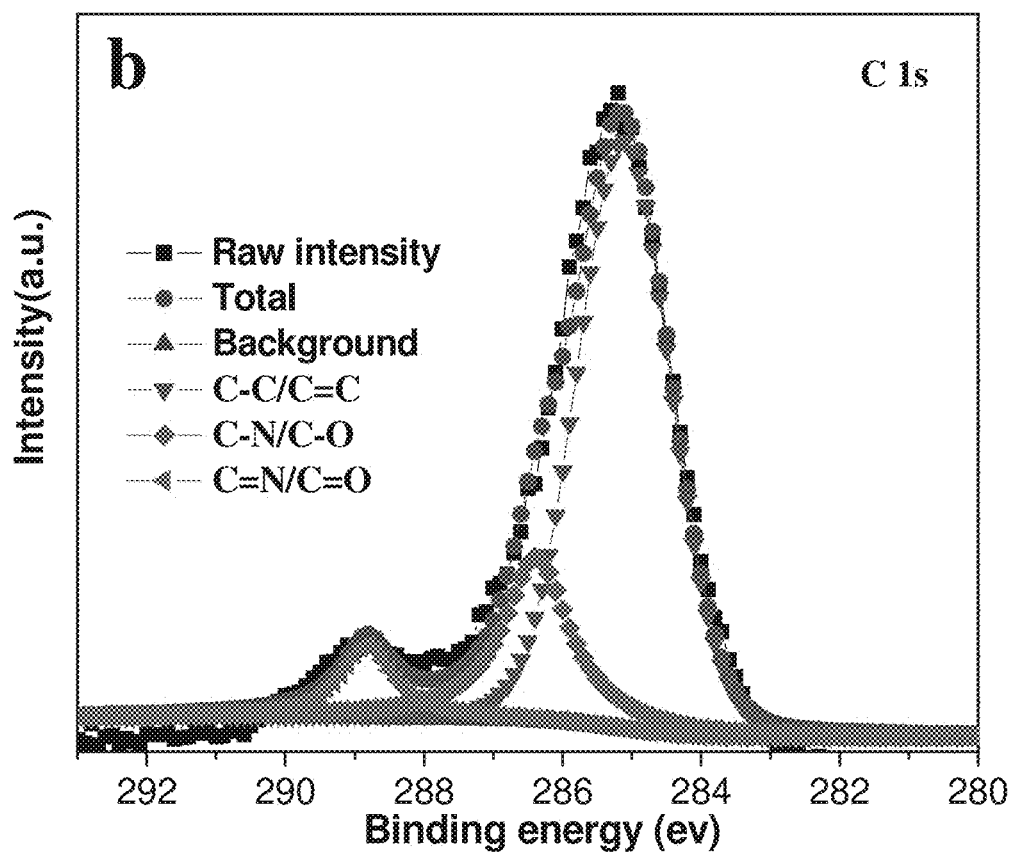
FIG. 2B shows an XPS survey spectrum of C1s for PCQDs.
Figure 2C:
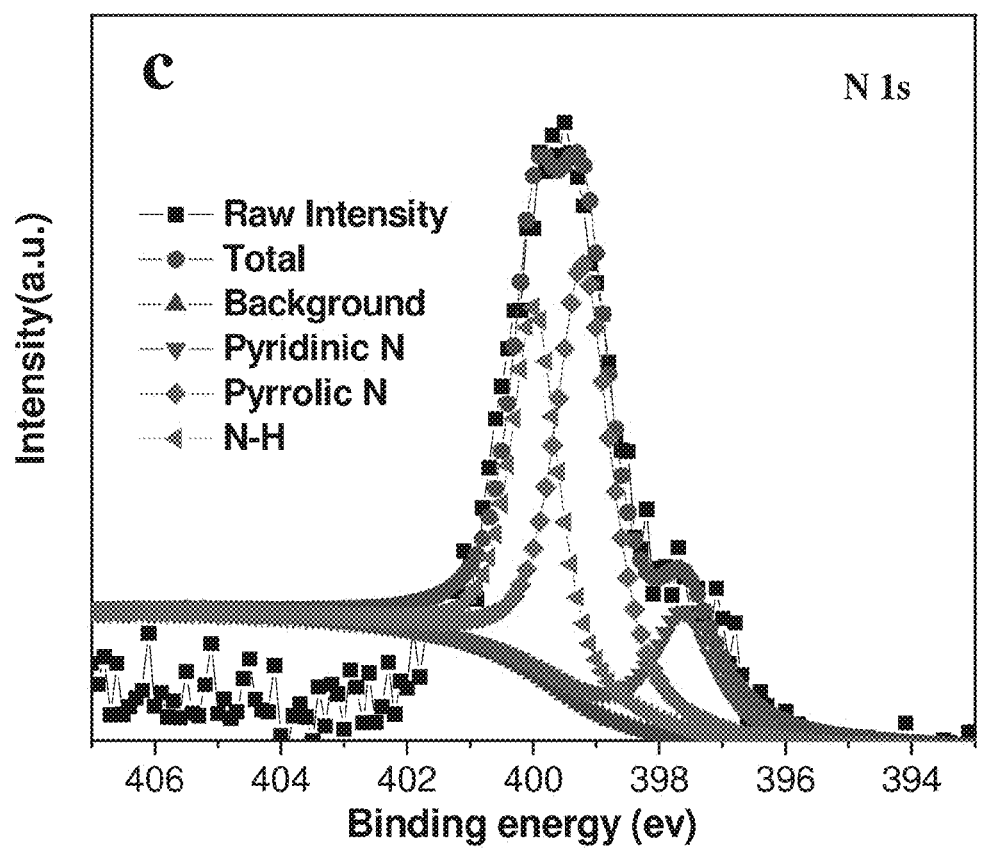
FIG. 2C shows an XPS survey spectrum of N1s for PCQDs.
Figure 2D:
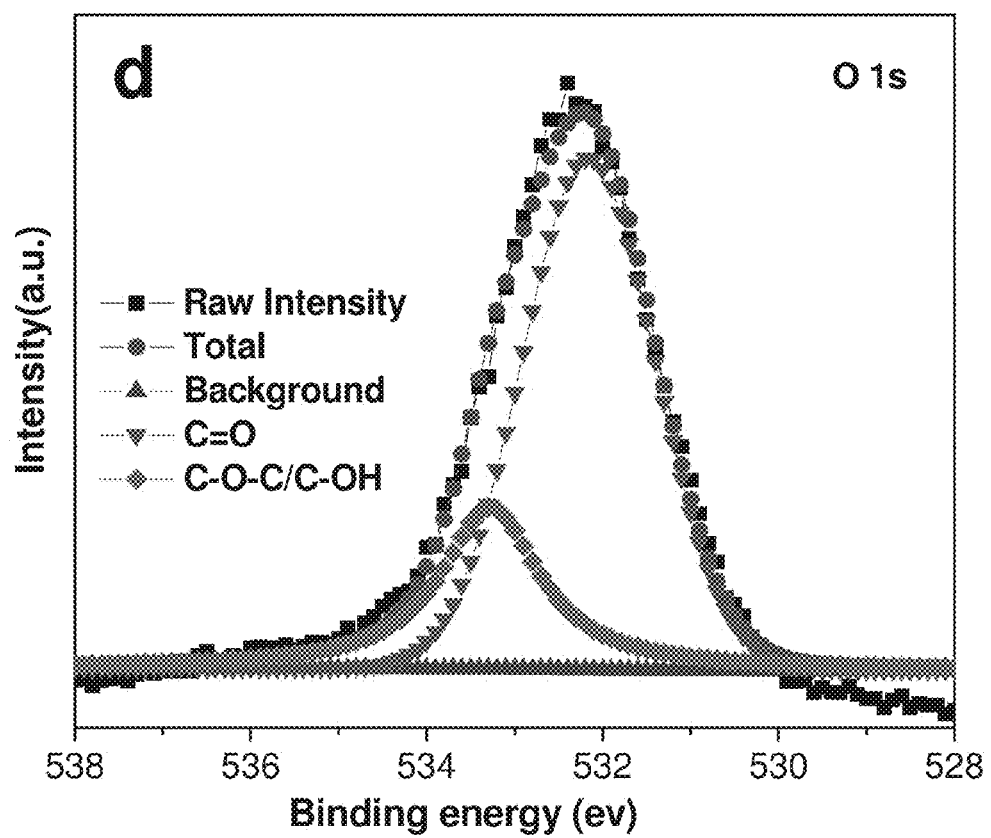
FIG. 2D shows an XPS survey spectrum of O1s for PCQDs.
Figure 2E:
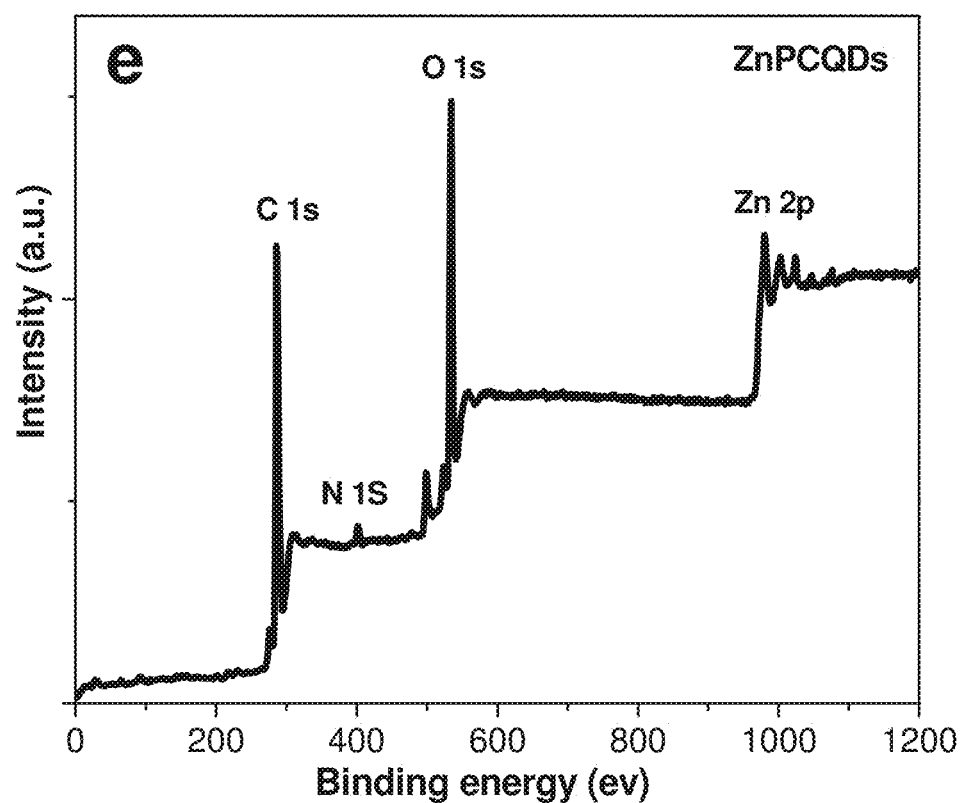
FIG. 2E shows an XPS survey spectrum of ZnPCQDs.
Figure 2F:
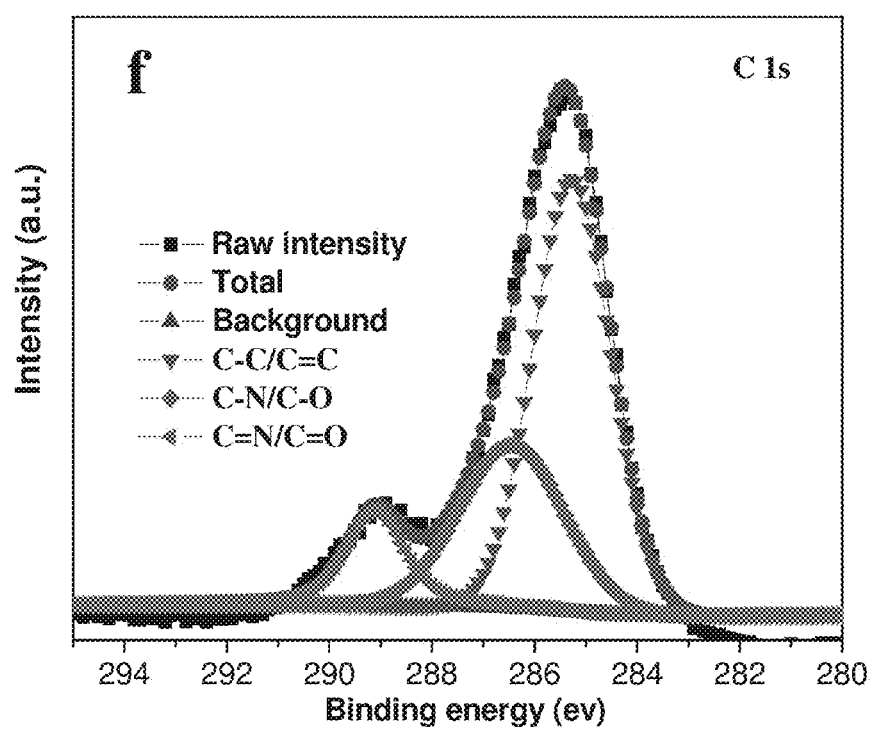
FIG. 2F shows an XPS survey spectrum of C1s for ZnPCQDs.
Figure 2G:
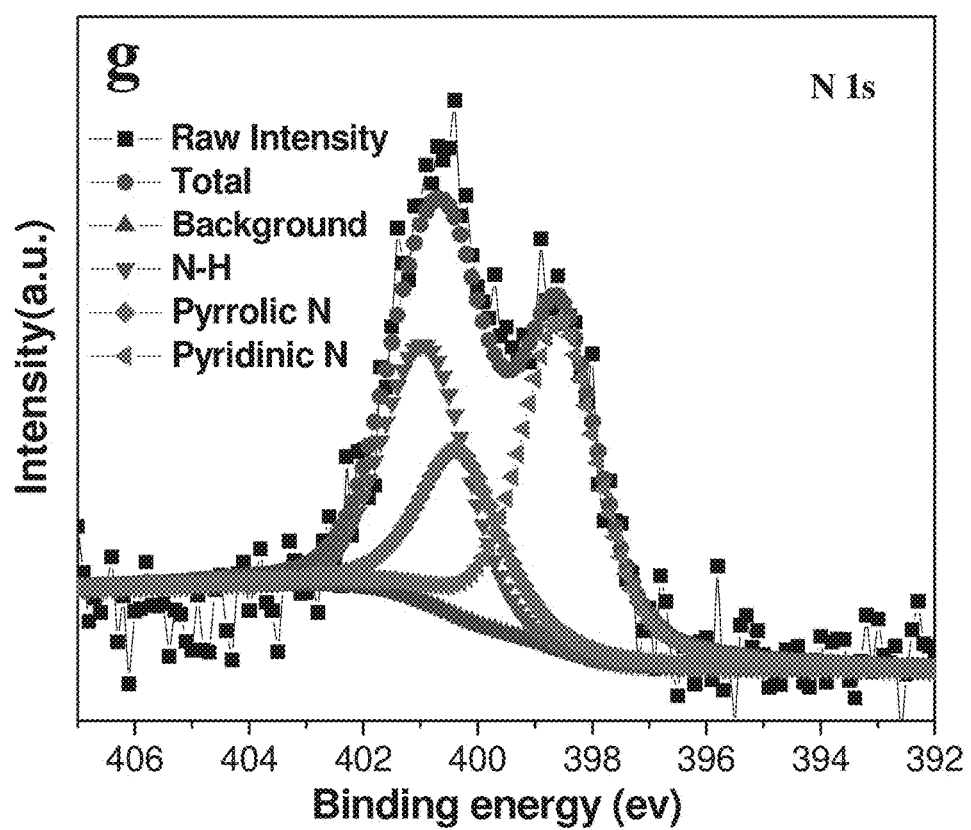
FIG. 2G shows an XPS survey spectrum of N1s for ZnPCQDs.
Figure 2H:
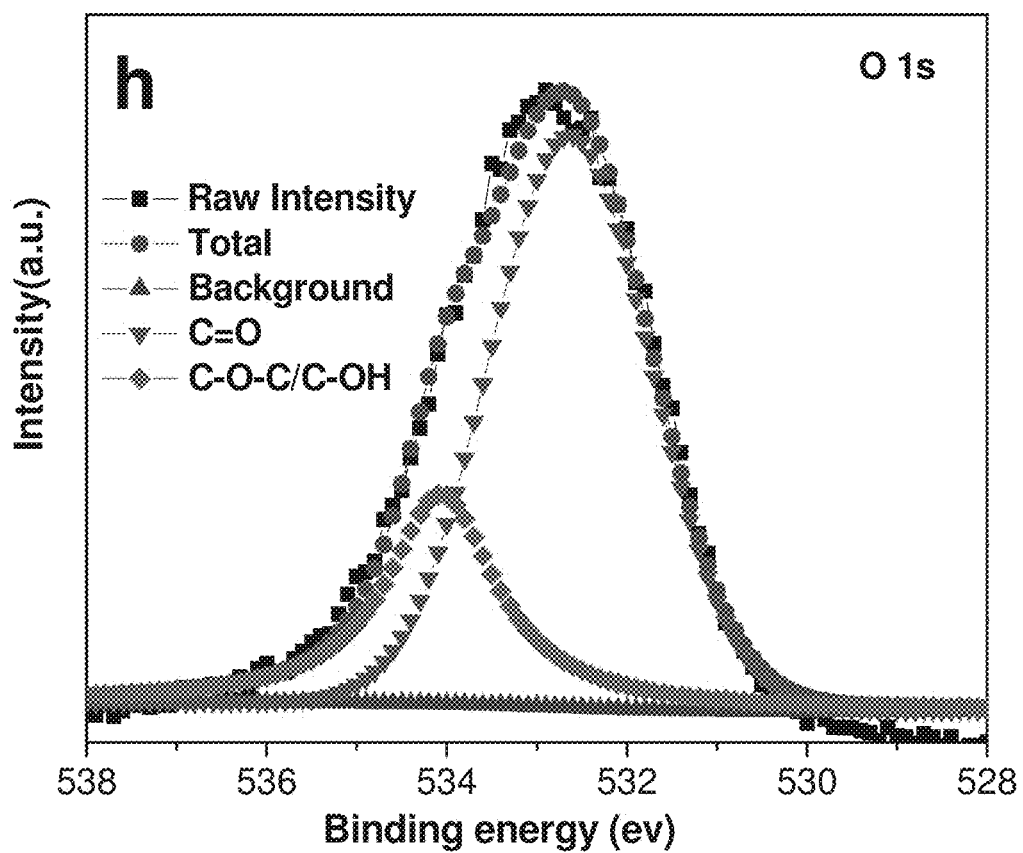
FIG. 2H shows an XPS survey spectrum of O1s for ZnPCQDs.
Figure 2I:
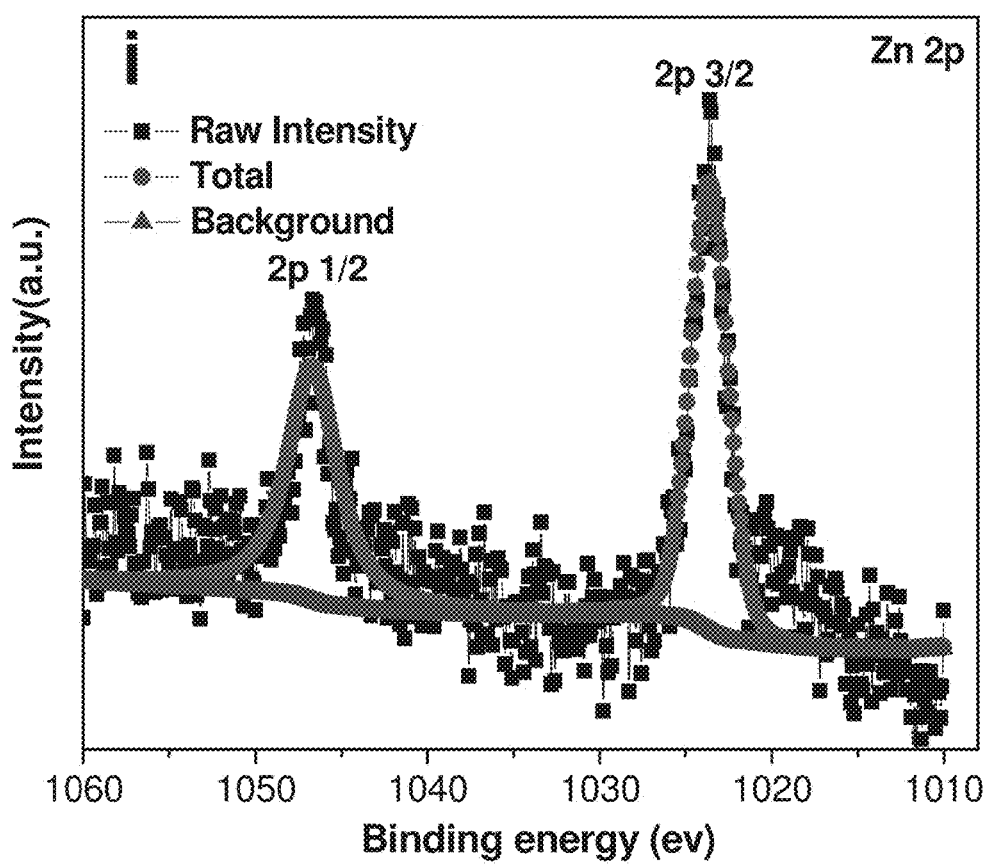
FIG. 2I shows an XPS survey spectrum of Zn 2p for ZnPCQDs.

The elemental composition and type of chemical bonds in the PCQDs and ZnPCQDs were confirmed by XPS as shown in FIGS. 2A and 2E. The peaks at 285.2, 400.8 and 532.7 eV are attributed to the C1s, N1s and O1s emissions, respectively. And the main peak in the high-resolution C1s XPS spectra of PCQDs and ZnPCQDs is observed at 285.1, 286.4 and 288.8 eV (FIGS. 2B and 2F), which is attributed to C—C/C═C, C—N,/C—O and C═O/C═N bonds, respectively. The high-resolution N1s spectrum of PCQDs and ZnPCQDs (FIGS. 2C and 2G) can be fitted to three peaks of pyridinic N (397.8 eV), pyrrolic N (399.2 eV) and quaternary N (400.7 eV). The high-resolution spectrum of O1s exhibits two peaks around 531.3 and 529.5 eV, which is attributed to C—OH/C—O—C and C═O (FIGS. 2D and 2H), respectively. The presence of oxygen-containing functional groups offers options for various types of surface modifications. Moreover, the XPS survey spectrum of ZnPCQDs shows the Zn 2p peaks, which further confirms the presence of zinc element in ZnPCQDs. The high resolution scans of the XPS spectra of Zn 2p (FIG. 2I) can be decomposed into two main components centered at 1023.7 and 1046.5 eV, corresponding to Zn $2p^{3/2}$ and Zn $2p^{1/2}$, respectively. The contents of C, N and Zn elements in ZnPCQDs are calculated to be 59.72%, 15.46% and 2.35%, respectively.

Figure 3A:
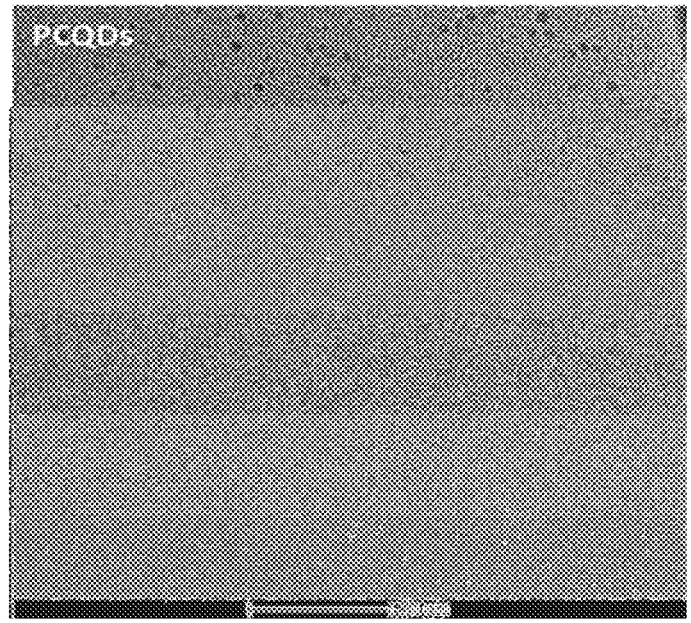
FIG. 3A shows a transmission electron microscopy TEM image of PCQDs.
Figure 3B:
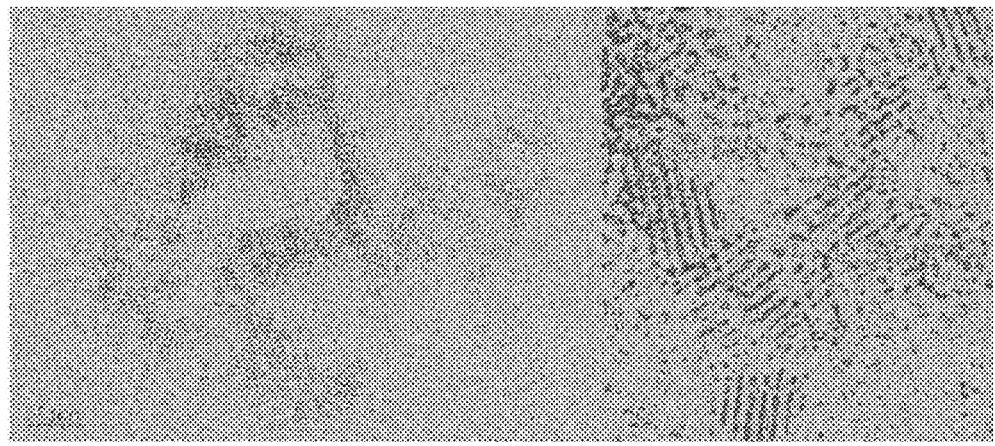
FIG. 3B shows a HRTEM image of PCQDs.
Figure 3C:
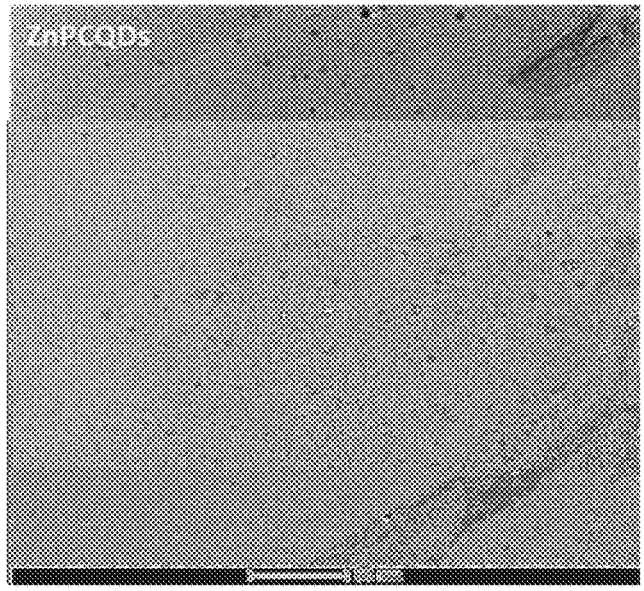
FIG. 3C shows a TEM image of ZnPCQDs.
Figure 3D:
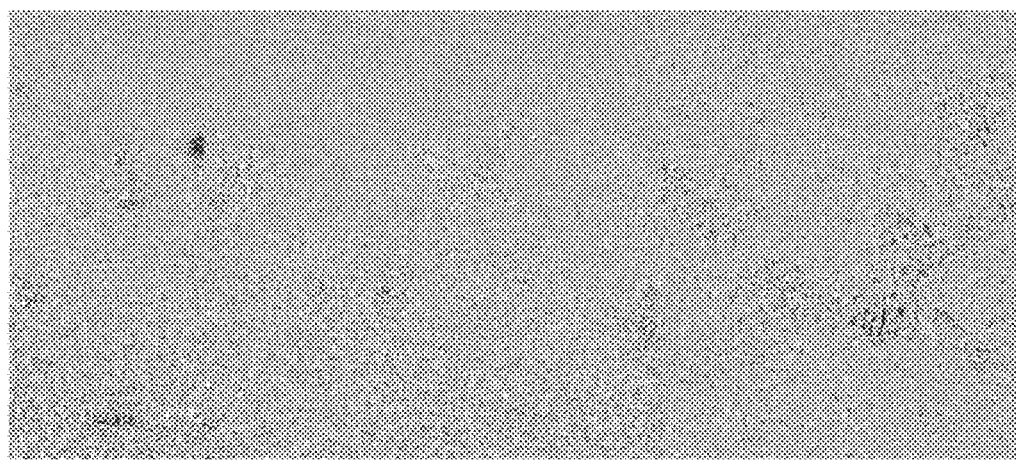
FIG. 3D shows a HRTEM image of ZnPCQDs.
Figure 4A:
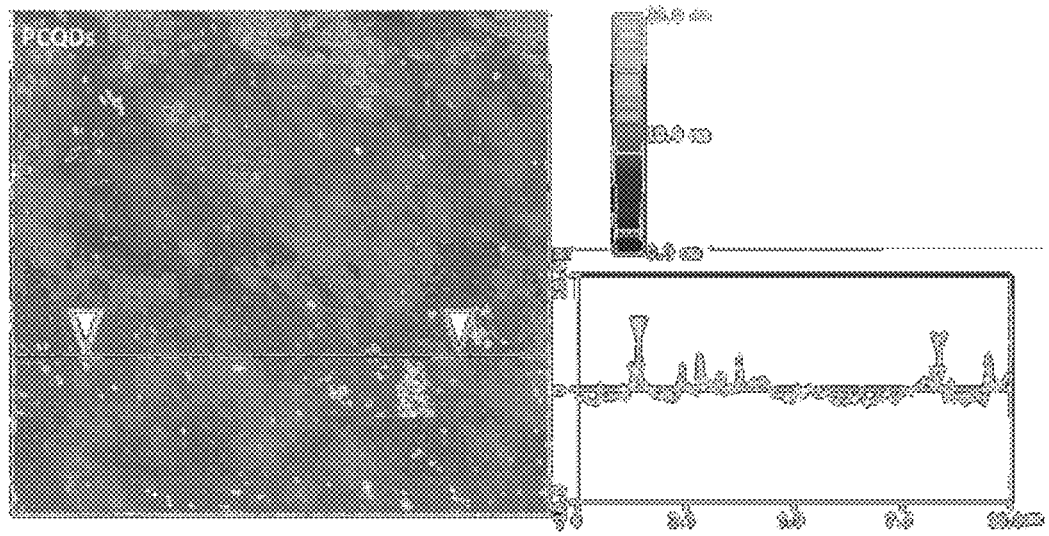
FIG. 4A shows height-mode AFM topography images of PCQDs with a line scan profile in the inset.
Figure 4B:
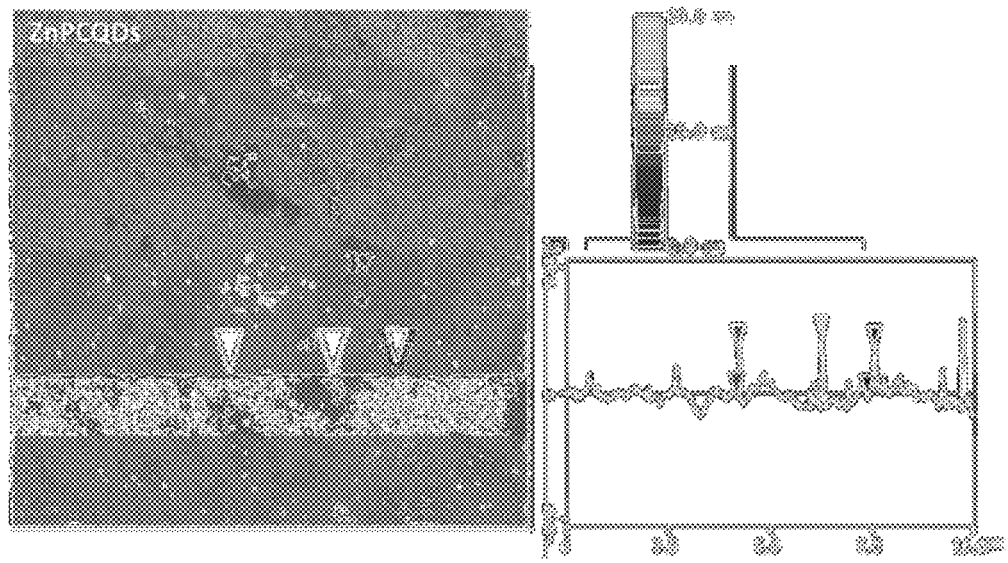
FIG. 4B shows height-mode AFM topography images of ZnPCQDs with a line scan profile in the inset.

The morphology of the PCQDs and ZnPCQDs was characterized using transmission electron microscopy (TEM) (FIGS. 3A, 3B, 3C and 3D) and atomic force microscopy (AFM) (FIGS. 4A and 4B). Drops of a dilute aqueous solution of porphyrin carbon quantum dots were deposited on a carbon-coated copper grid for TEM and on glass and silicon substrates for AFM. As shown in FIGS. 3A and 3C, the porphyrin carbon quantum dots are spherical and well dispersed with an average diameter of 3.3 nm and 3.4 nm for PCQDs and ZnPCQDs, respectively. Well-resolved lattice fringes are observed from the high-resolution TEM images, corresponding to d spacing values of 0.28 and 0.32 nm, which are close to the (020) and (002) planes of graphitic carbon, respectively. The AFM images of PCQDs and ZnPCQDs are shown in FIGS. 4A and 4B, from which we can see that the topographic height of PCQDs is distributed in the range of 1.2 to 4.5 nm with an average height of 3.7 nm, while the average height of ZnPCQDs is 4.3 nm. Specifically, the size of PCQDs from TEM are somewhat smaller than the overall dot profiles estimated from the height analysis of AFM images, indicating the latter may also include contributions of the porphyrin molecules on carbon particle surface that survived during the process of thermal carbonization.

Figure 5A:
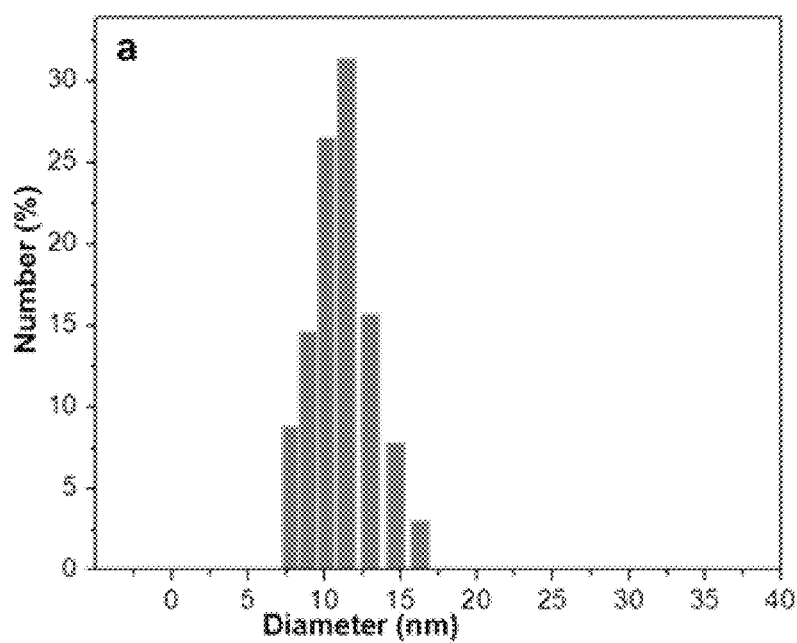
FIG. 5A shows dynamic light scattering (DLS) of C225-PCQDs in water.
Figure 5B:
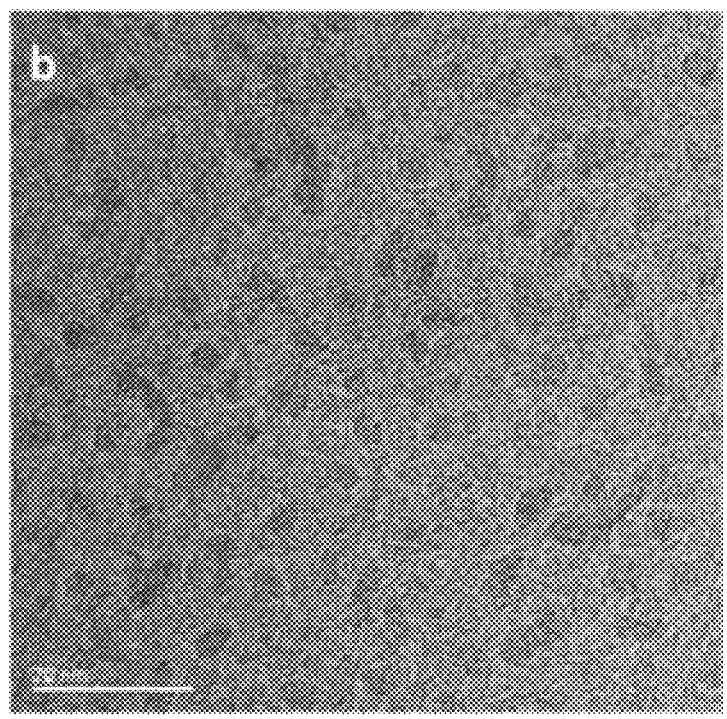
FIG. 5B shows a TEM image of C225-PCQDs.

The morphology of C225-PCQDs was also investigated by high resolution TEM, and their size distribution was studied with dynamic light scattering (DLS). As shown in FIGS. 5A and 5B, the size of C225-PCQDs from TEM image (FIG. 5B) is around 10 nm, which is well consistent with DLS analysis (~11.4±3.5 nm) (FIG. 5A). The larger size of nanoparticle after the conjugation with C225 indicates the antibody molecules was coated over the surface of porphyrin carbon quantum dots.

Figure 6:
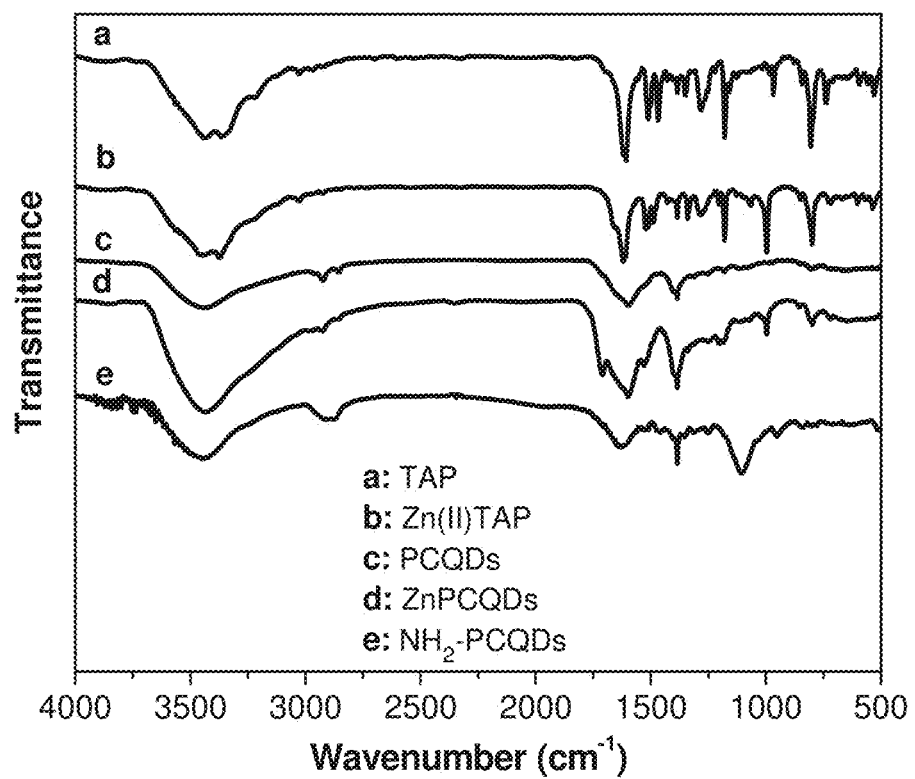
FIG. 6 shows FT-IR spectra of PCQDs and ZnPCQDs.

The surface functional groups of PCQDs, ZnPCQDs, and NH$_2$-PCQDs were also demonstrated by their FT-IR spectra. As shown in FIG. 6, the broad absorption bands located at 3427 cm$^{-1}$ are assigned to v(O—H) and v(N—H). A small band at 2925 cm$^{-1}$ is attributed to the C—H bonds. These functional groups improve the hydrophilicity and stability of the porphyrin carbon quantum dots in aqueous systems. The band at 1720 cm$^{-1}$ is assigned to C=O stretching vibrations. Besides, the asymmetric and symmetric C—O—C stretching vibrations (1315 and 1189 cm$^{-1}$, respectively) are detected. The peaks at 1524 and 1663 cm$^{-1}$ are assigned to amide stretching vibrations, and the peak at 1445 cm$^{-1}$ is attributed to the amide C—N stretch.

Photophysical and Photochemical Properties.

Figure 7A:
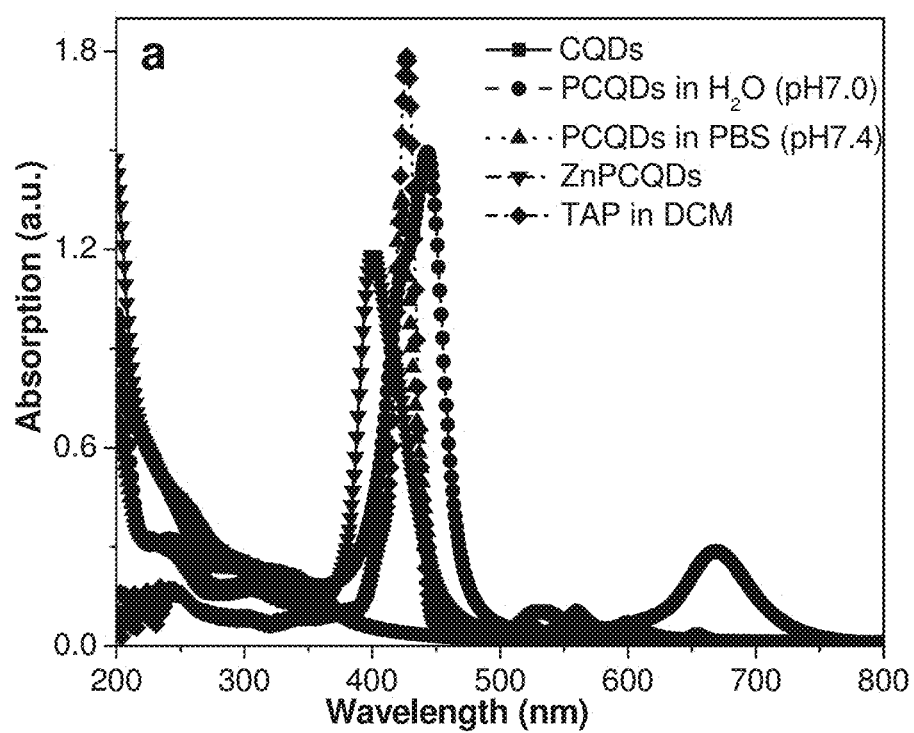
FIG. 7A shows UV-vis absorbance spectra of PCQDs in water and alkaline buffer.

The as-prepared PCQDs and ZnPCQDs are dispersed well in water. The presence of porphyrin ring or its zinc complex in the carbon quantum dots was also confirmed by UV-vis spectroscopy. As shown in FIG. 7A, the absorption of PCQDs in water shows a broad signal from 200 to 400 nm from the carbon quantum dots, and a Soret band at 450 nm and Q-bands around 650 nm apparently attributed to the existence of porphyrin ring. In addition, the red-shifted Soret and Q-bands and also signal intensified Q-bands of PCQDs in water suggests that encapsulated porphyrin ring was fully protonated by carboxylic acid groups on the surface of carbon quantum dots. As expected, upon the addition of a drop of aqueous ammonia into the solution of PCQDs, the pH values indicates a slightly alkaline environment, and the Soret band will shift back to 423 nm together with the change of color from green to red. While, the UV absorbance of ZnPCQDs exhibits a fixed Soret band at 420 nm no matter it dissolved in water or alkaline buffer because of the inserted metal in the porphyrin core.

Figure 5C:
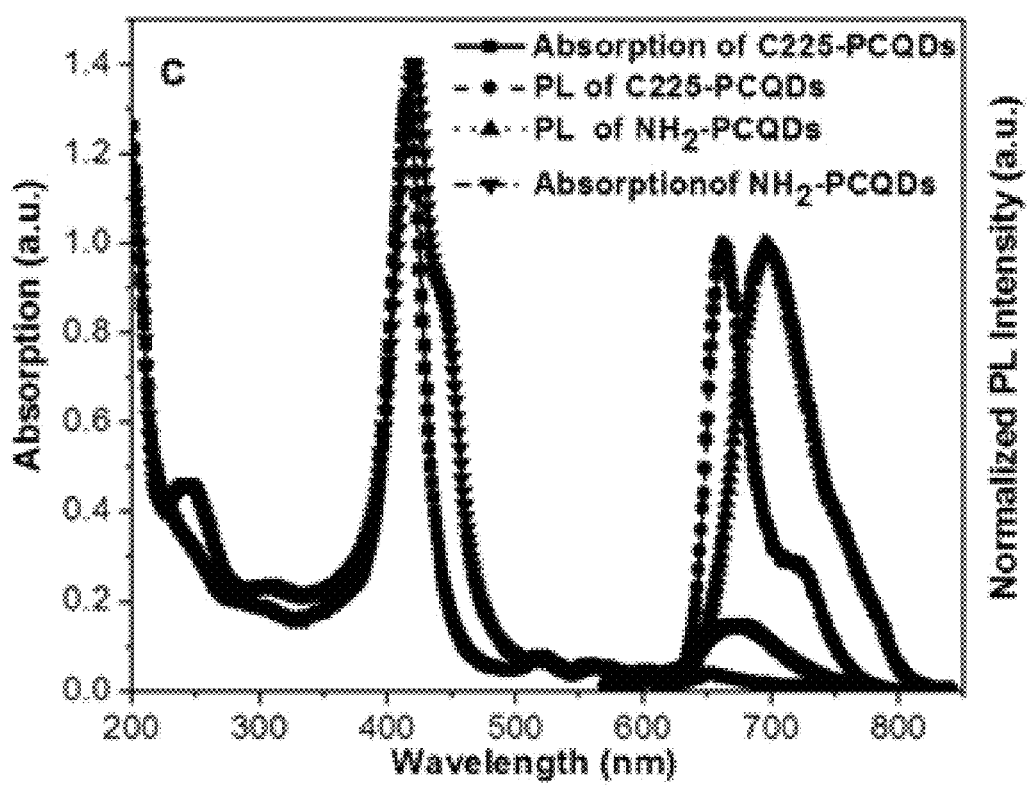
FIG. 5C shows UV-vis absorption (solid line) and emission spectra (dash line) of $NH_2$-PCQDs and C225-PCQDs in water.
Figure 7B:
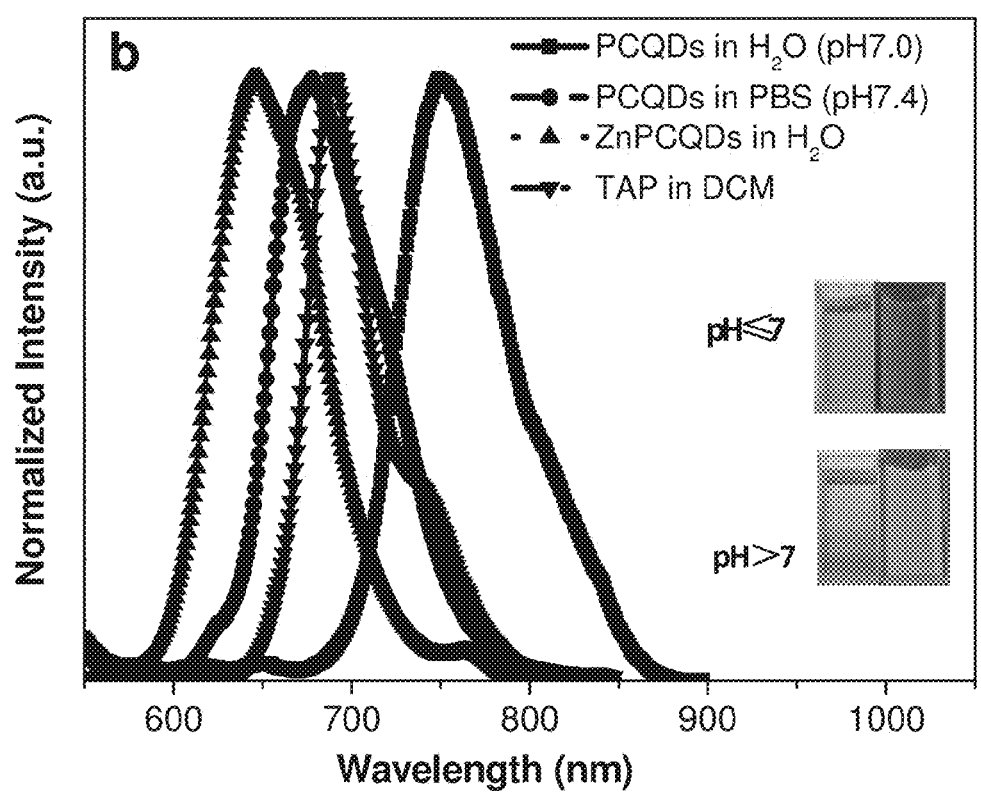
FIG. 7B shows Emission spectra of PCQDs, ZnPCQDs and TAPP (excitation: 440 nm).

Upon the excitation at 440 nm, the aqueous solution of PCQDs and ZnPCQDs display an intense red emission with maximum peaks at 750 and 647 nm (FIG. 7B), respectively. At the same time, the pH value of solution has a significant effect on the photoluminescence of PCQDs. As shown in the insert of FIG. 7B, PCQDs in PBS buffer (pH=7.4) displays a remarkably stronger red emission than that in water (pH=7.0), with the maximum peak changed from 678 to 750 nm, which is also consistent with the equilibrium nature of the protonation mechanism of porphyrin. On the other side, the photoluminescence of ZnPCQDs doesn't show any variation with the change of pH values because of the complexation of Zn(II) metal. After the functionalization with poly(ethylene glycol)diamine and sequent conjugation with cetuximab, the absorption and emission spectrum of materials (NH$_2$-PCQDs and C225-PCQDs) don't show any significant change related to that of PCQDs, as shown in FIG. 5C.

Figure 8A:
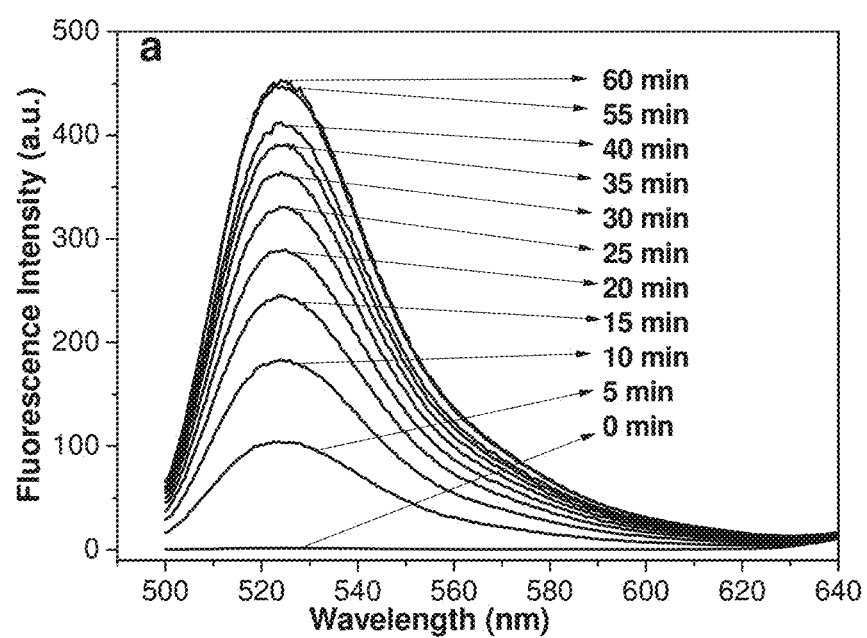
FIG. 8A shows emission spectra of DCFH solution in the presence of PCQDs with the increase of irradiation time.
Figure 8B:
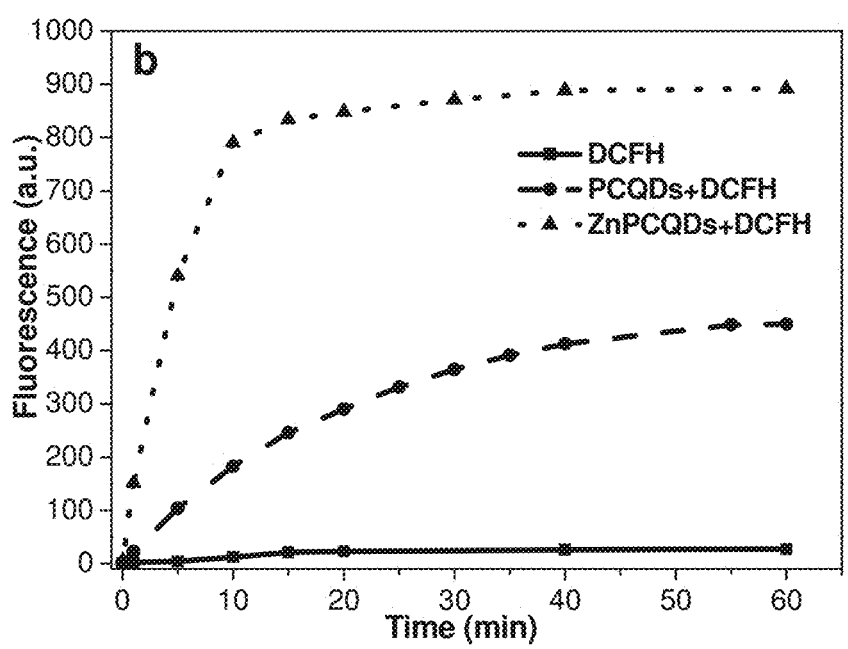
FIG. 8B shows changes of fluorescence intensity at the characteristic peak of DCFH (525 nm) as a function of laser irradiation time.

Subsequently, the generation of reactive oxygen species (ROS) via photoinduced energy transfer from PCQDs and ZnPCQDs was quantified using the dichlorofluorescin (DCFH) reagent. The green fluorescence ($\lambda_{em}$=525 nm) of DCFH is known to increase quantitatively when it reacts with ROS generated from the porphyrin. As shown in FIG. 8A, the fluorescence intensity of DCFH's exhibits a time-dependent enhancement after reaction with ROS, generated from PCQDs and ZnPCQDs upon irradiation with a 500 W Xe lamp (6.5 mW/cm$^2$). While, the ZnPCQDs reveals a more effective generation of ROS than that of PCQDs (FIG. 8B), which could be attributed to the increased intersystem crossing efficiency in the case of metal complexation. The results further demonstrate that the ROS was mainly produced by porphyrins encapsulated in carbon quantum dots.

In Vitro Imaging and PDT.

Figure 9A:
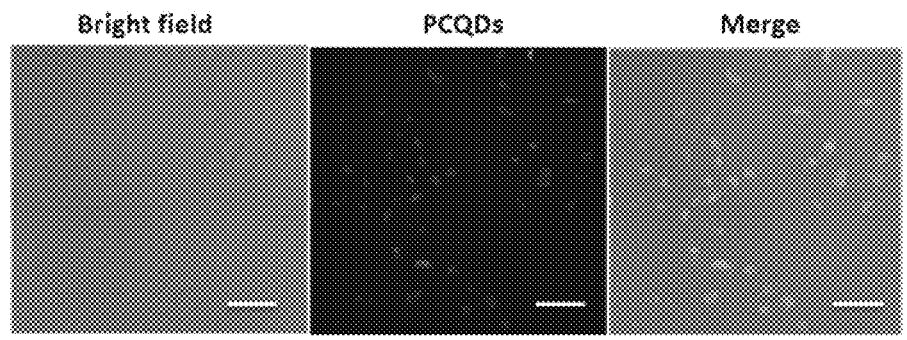
FIG. 9A shows laser scanning confocal microscopy images of HeLa cells incubated with PCQDs at a concentration of 0.5 mg/mL in the cell culture medium for 24 h at 37° C. (The scale bar is 20 μm).
Figure 9B:
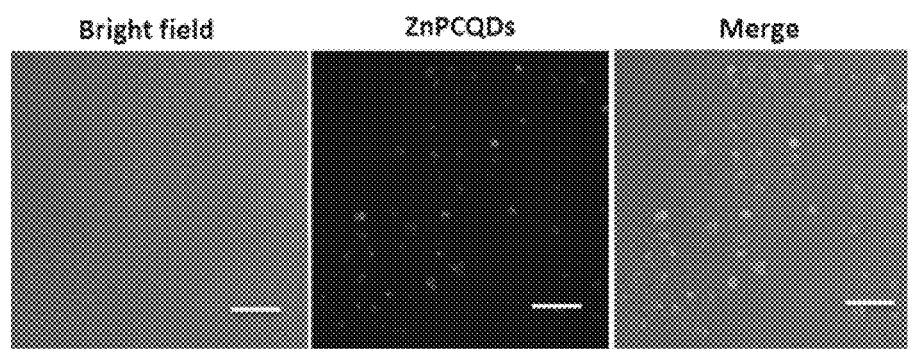
FIG. 9B shows laser scanning confocal microscopy images of HeLa cells incubated with ZnPCQDs at a concentration of 0.5 mg/mL in the cell culture medium for 24 hours at 37° C. (The scale bar is 20 μm).

To investigate the cellular uptake and subcellular localization of PCQDs and ZnPCQDs, fluorescence imaging was performed on human HeLa cells using a confocal laser scanning microscope (FIGS. 9A and 9B). After 24 hours incubation with 0.5 mg/mL PCQDs and ZnPCQDs, the HeLa cells displayed an intense red fluorescence in cytoplasm, indicating the accumulation of PCQDs and ZnPCQDs in cells.

Figure 10A:
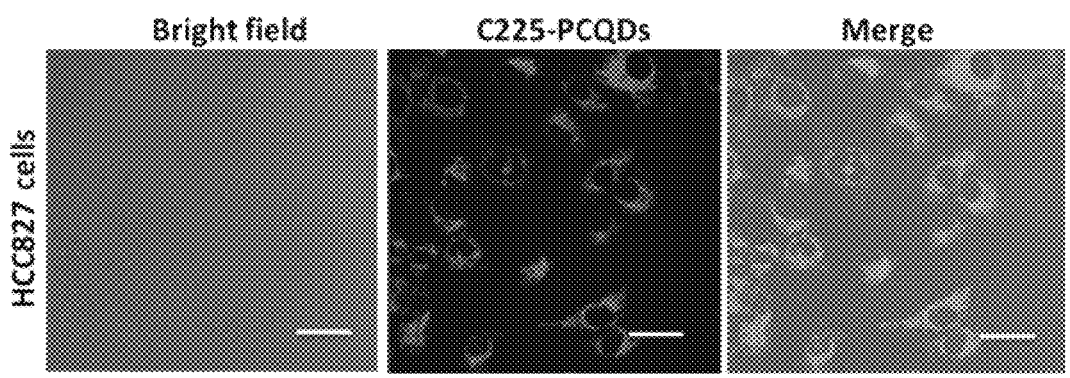
FIG. 10A shows laser scanning confocal microscopy images of HCC827 cells incubated with C225-PCQDs at a concentration of 0.5 mg/mL in the cell culture medium for 12 hours at 37° C. (the scale bar is 20 μm).
Figure 10B:
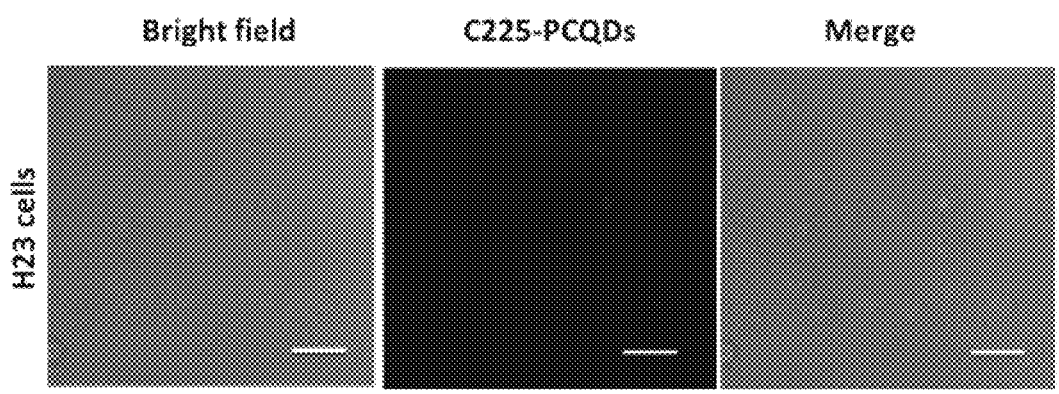
FIG. 10B shows laser scanning confocal microscopy images of H23 cells incubated with C225-PCQDs at a concentration of 0.5 mg/mL in the cell culture medium for 12 hours at 37° C. (the scale bar is 20 μm).

Next to evaluate the targeting ability of cetuximab-conjugated porphyrin carbon quantum dots, C225-PCQDs was incubated with HCC827 and H23 cells at 0.5 mg/mL for 12 hours, respectively, and then analyzed by confocal laser scanning microscope. As shown in FIGS. 10A and 10B, the HCC827 cells incubated with C225-PCQDs (the first row) displayed strong red fluorescent signals. In contrast, only a very weak red fluorescent signals could be observed in H23 cells when treated with C225-PCQDs under the same condition (the second row), indicating the cetuximab-conjugated PCQDs could target specifically the cancer cells with over-expression of EGFR via EGFR mediated endocytosis.

Figure 11A:
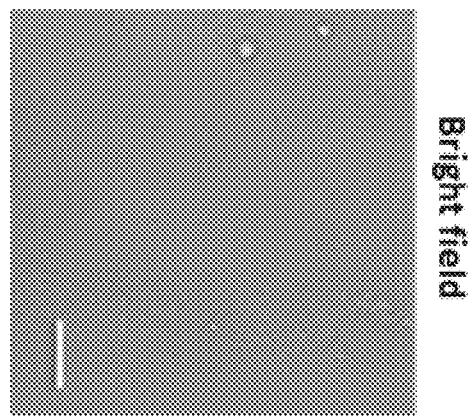
FIG. 11A shows Bright-field of HCC827 cells (the scale bar is 20 μm).
Figure 11B:
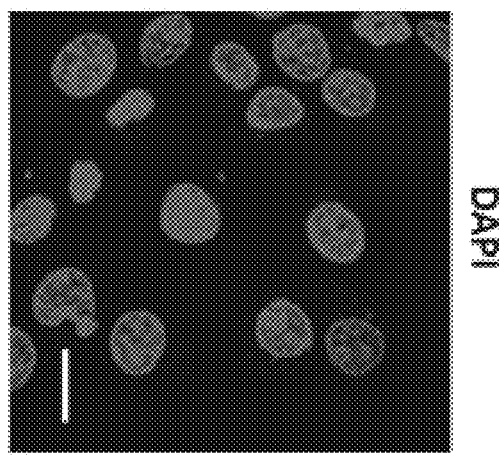
FIG. 11B shows the nucleus (blue) was stained with DAPI (10 μg/mL) (the scale bar is 20 μm).
Figure 11C:
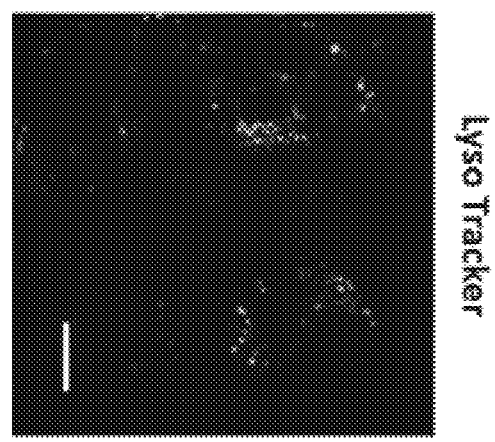
FIG. 11C shows lysosomes (green) were stained with LysoTracker® Green DND-26 (75 μM) (the scale bar is 20 μm).
Figure 11D:
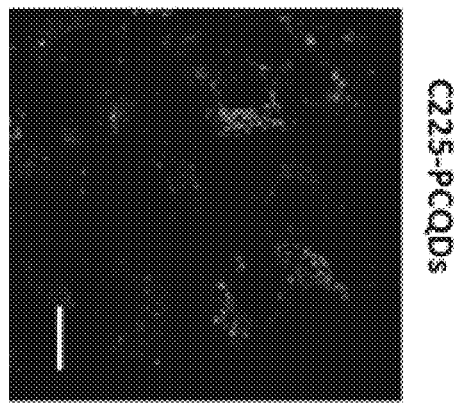
FIG. 11D shows laser scanning confocal microscopy images of HCC827 cells incubated with C225-PCQDs for 12 hours (the scale bar is 20 μm).
Figure 11E:
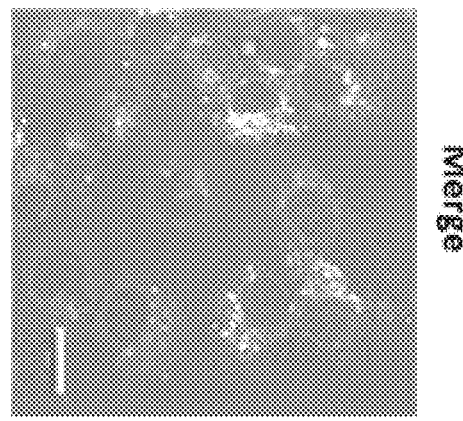
FIG. 11E shows the merge images of FIGS. 11A-11D (the scale bar is 20 μm).

To further figure out the localization of C225-PCQDs in HCC827 cells, DAPI and LysoTracker® Green DND-26 staining were applied to visualize cell nuclei and lysosome, respectively. As shown in FIG. 11A-11E, the blue fluorescence representing the nuclei stained by DAPI (FIG. 11B) are surrounded by red fluorescence from that of C225-PCQDs (FIG. 11D), which are perfectly overlaps with that of green fluorescence of DND-26 (FIG. 11C), indicating the cetuximab-conjugated porphyrin carbon quantum dots are localized primarily in the lysosomes of cells. FIG. 11A shows the bright-field of HCC827 cells and FIG. 11E shows the merge images of FIG. 11A, FIG. 11B, FIG. 11C and FIG. 11D.

Figure 12A:
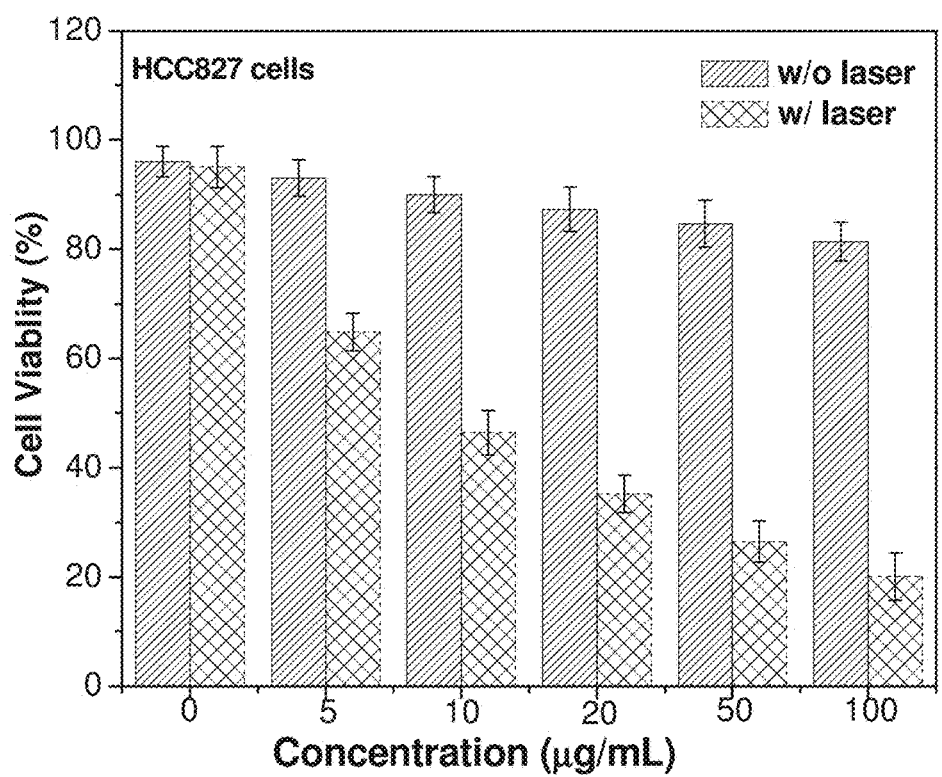
FIG. 12A shows HCC827 cells viability at different concentrations of C225-PCQDs for 24 hours at 37° C. without or with irradiation for 30 min with a 500 W Xe lamp (6.5 mW/cm$^2$).
Figure 13A:
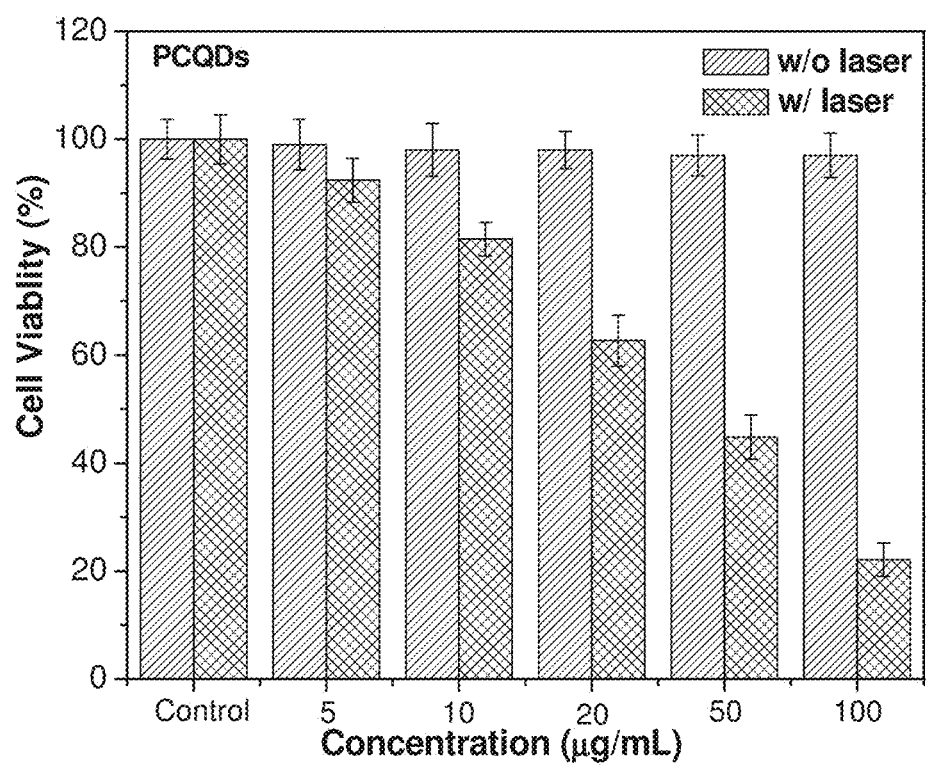
FIG. 13A shows HeLa cells viability at different concentrations of PCQDs for 24 h at 37° C. with or without irradiation for 30 min with a 500 W Xe lamp (6.5 mW/cm$^2$).
Figure 13B:
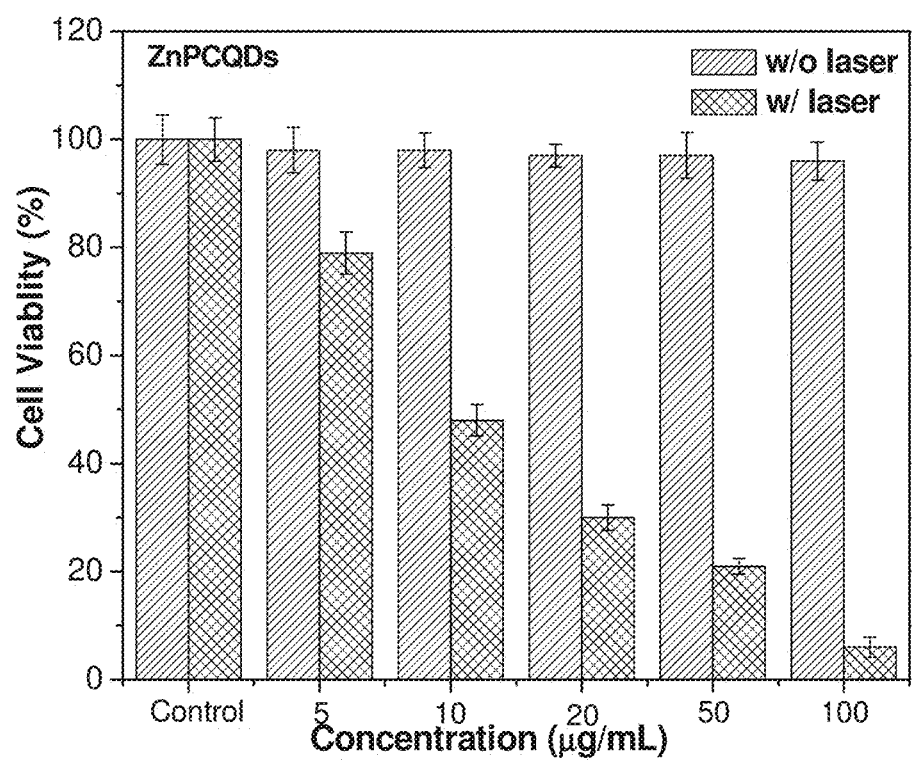
FIG. 13B shows HeLa cells viability at different concentrations of ZnPCQDs for 24 h at 37° C. with or without irradiation for 30 min with a 500 W Xe lamp (6.5 mW/cm$^2$).

Afterwards, the potential photodynamic cytotoxicity of C225-PCQDs was evaluated through an in vitro CCK-8 assay. As shown in FIG. 12A, the PDT effect of C225-PCQDs was evaluated in the concentration range of 0-100 µg/mL on tumor HCC827 cells. Cell viability was normalized to control cells (no drug and non-irradiated). Exposure of tumor cells to C225-PCQDs for 24 hours followed by laser irradiation induced a concentration-dependent cytotoxicity to HCC827 cells. The cell viabilities of C225-PCQDs with irradiation were determined to be 22.3% at a concentration of 100 g/mL. However, over 85% of cells still survived upon exposure to C225-PCQDs without irradiation, indicating the C225-PCQDs alone had no adverse effect on tumor cells. Moreover, the cytotoxicity of porphyrin carbon quantum dots on HeLa cells revealed the stronger PDT effect of ZnPCQDs than that of PCQDs upon irradiation (FIGS. 13A and 13B), which was in agreement with the trends of ROS generation as mentioned above.

Figure 12B:
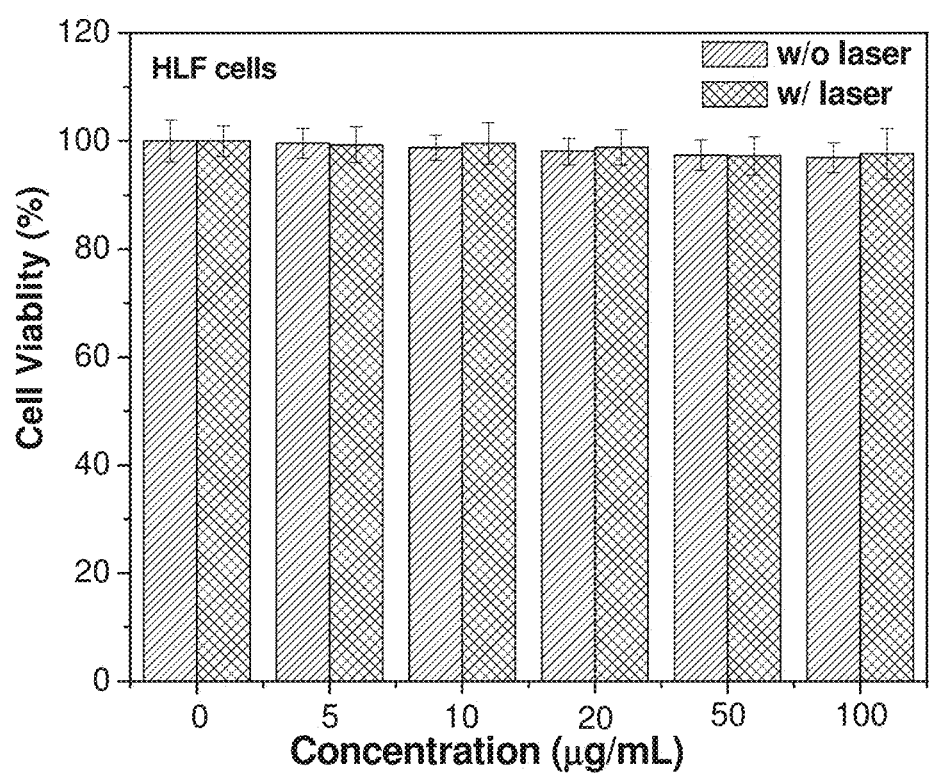
FIG. 12B shows HLF cells viability at different concentrations of C225-PCQDs for 24 hours at 37° C. without or with irradiation for 30 min with a 500 W Xe lamp (6.5 mW/cm$^2$).

The combination of 24 hour exposure of normal HLF cells (FIG. 12B) to C225-PCQDs and laser irradiation induced no significant cytotoxicity to HLF cells, which was almost same with the non-irradiated controls, indicating that C225-PCQDs had no effects on normal cells whether in dark or upon exposure to light. This result is evidence of the selective uptake of C225-PCQDs in HCC827 cells because of the over-expression of EGFR, demonstrating that C225-PCQDs can be used for targeting delivery of porphyrin into the tumor cells with over-expression of EGFR, and reducing the accumulation of nanoscale drugs in normal cells.

Figure 14A:
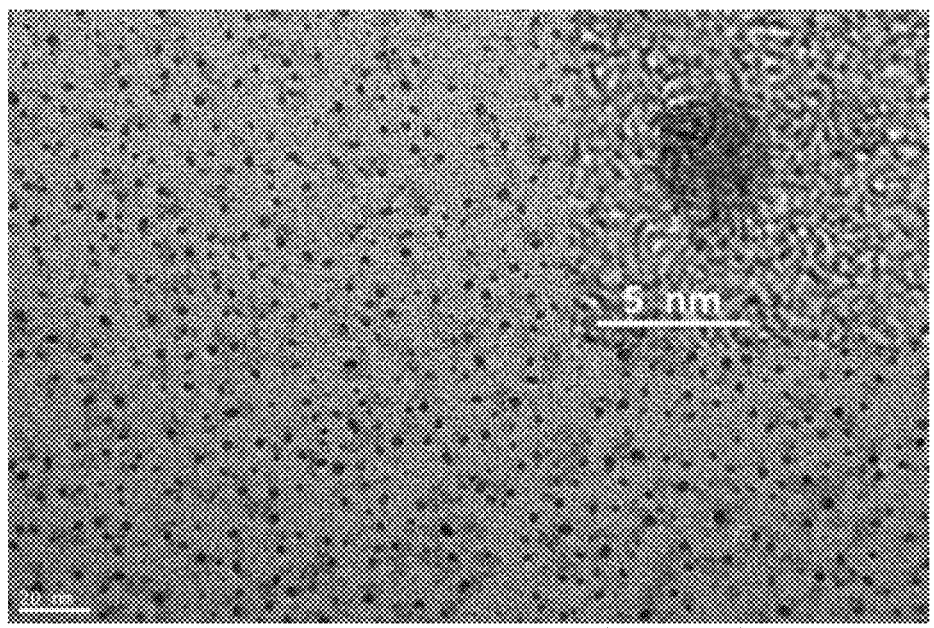
FIG. 14A shows TEM images of CQDs absorption, excitation and fluorescence spectra of CQDs.

FIG. 14A shows the typical transmission electron microscopy (TEM) images of CQDs. The TEM images confirmed the formation of CQDs and revealed that the as-synthesized colourless CQDs have a relatively narrow size distribution ranging from 2 to 4 nm with an average diameter of 3 nm.

The high-resolution TEM (HRTEM) images are shown in insert FIG. 14A. It can be seen that the as-prepared CQDs were of high crystallinity and the lattice spacing was around 0.31 nm in the crystalline structures of the CQDs, which agrees well with the <002> spacing of graphitic carbon. Similar to other CQDs reported elsewhere, the CQD solution exhibited strong luminescence.

Figure 14B:
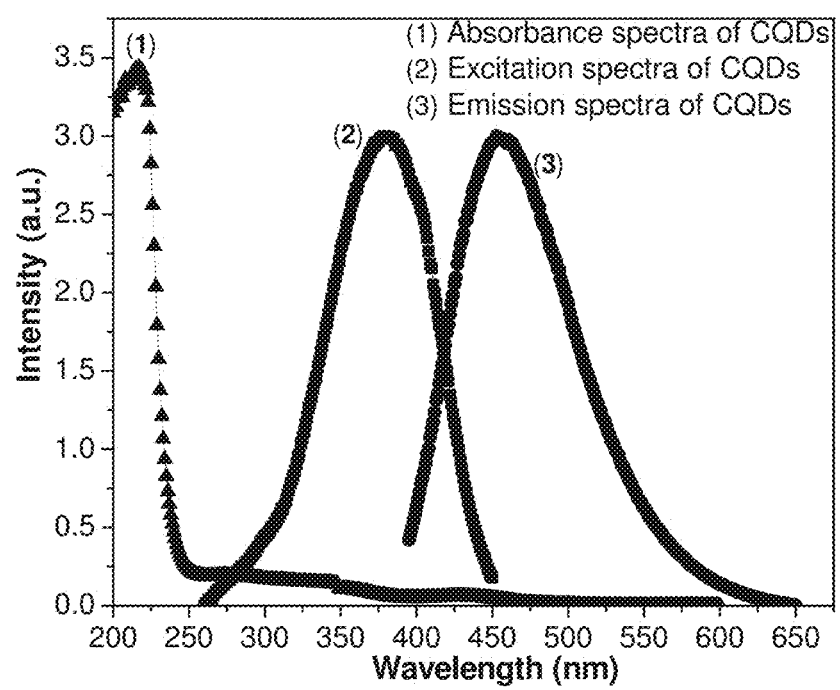
FIG. 14B shows UV-vis absorption, excitation and fluorescence spectra of CQDs.

FIG. 14B shows the UV-vis absorption, photoluminescent (PL) emission spectra and excitation spectrum of the CQDs aqueous solution. The UV-vis absorption spectrum of the CQDs shows the strong absorption below 300 nm with maximum peak at approximately 220 nm, which is mainly attributed to the π-π* transitions of aromatic sp2 domains. Moreover, the weak absorption tail between 300 and 400 nm was also observed, corresponding n-π* transitions of heteroatom (N and O)-containing bonds. The PL emission with a peak at around 460 nm was observed for the aqueous dispersion of CQDs under excitation at 360 nm (FIG. 14B).

Discussion

Porphyrin carbon quantum dots (e.g., PCQDs and ZnPCQDs) were prepared by a one-pot hydrothermal method, with citric acid (CA) as the carbon precursor and tetraaminoporphyrins as the passivation agent. The porphyrin or its metal complex was encapsulated in the core of carbon quantum dots during the process of preparation. Their structures were well established by UV-Vis spectra, PL spectra, FT-IR, TEM and AFM analyses, which both exhibit an intense red emission, good aqueous dispersibility and favorable biocompatibility. The in vitro PDT results on HeLa cells through CCK-8 assay indicated that the prepared PCQDs or ZnPCQDs alone had no adverse effect on tumor cells, but displayed remarkable photodynamic efficacy upon the irradiation.

Figure 15:
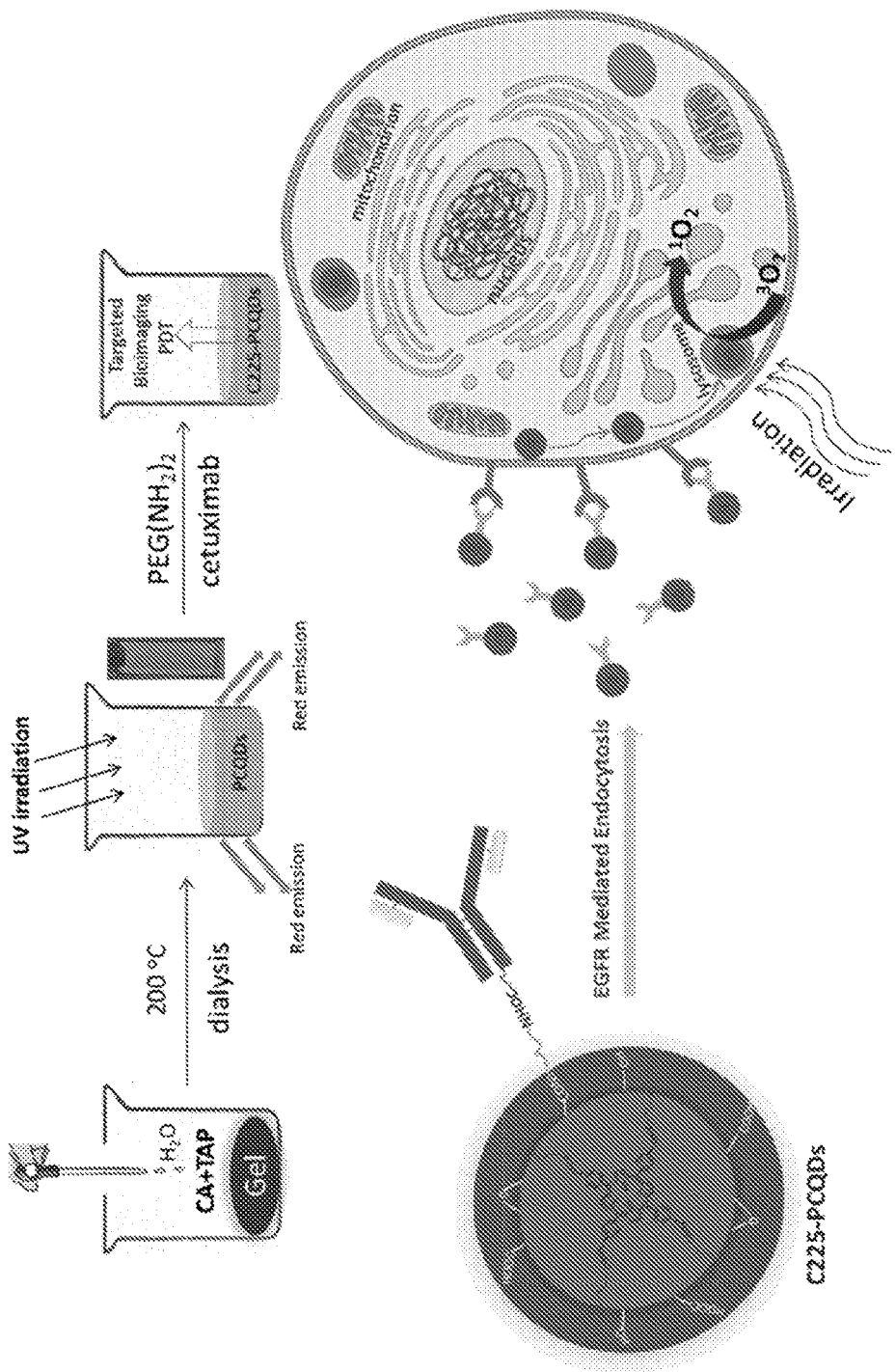
FIG. 15 shows the formation and PDT procedure of C225-PCQDs.

Subsequently, the surface of PCQDs was functionalized with poly(ethylene glycol) diamine to acquire $NH_2$-PCQDs, and then conjugated with cetuximab to afford C225-PCQDs. In comparison with cells with low expression of EGFR (H23 cells), the C225-PCQDs could target specifically the non-small lung cancer cells with over-expression of EGFR (HCC827 cells) via EGFR mediated endocytosis as analyzed by confocal laser scanning microscope (FIGS. 10A and 10B). The subcellular localization experiment of C225-PCQDs in HCC827 cells indicates its lysosome-targeting performance. Accordingly, the C225-PCQDs can significantly increase the accumulation of photosensitizer in the HCC827 cells and lead to a remarkable photodynamic effect. Definitely, the inventors successfully developed the C225-PCQDs with good biocompatibility and efficient PDT effect upon specific cancer cells. The novel drug delivery system based on cetuximab-conjugated porphyrin carbon quantum dots provided a simple and feasible modality to develop the targeted nanomedicine for practical PDT applications (FIG. 15).

Methods

Synthesis of PCQDs and ZnPCQDs.

The synthetic strategy and proposed formation pathway of PCQDs are shown in FIG. 16 and FIG. 17, respectively. In a typical synthetic procedure, 0.1 g tetraamino-porphyrin (TAP) and 1.0 g organic acid (OA) were dissolved in 20 mL DI water, and then sonicated for 10 min at room temperature. The uniform solution was heated to 180-220° C. with a heating mantle. When the gel was formed, 2 mL of DI water was added to prevent it from scorching and heating was continued. The same procedure was repeated for 3 hours. After the reaction, the obtained PCQDs was cooled to room temperature and dispersed in 10 mL DI water. The resulting dark brown solution was centrifuged at 15,000 rpm for 30 min to remove weight precipitate and agglomerated particles and then was dialyzed against DI water for three days, yielding a green aqueous solution of PCQDs. The solid product was collected after freeze-drying and could be dissolved again in water for further characterization and use. The ZnPCQDs was prepared with the similar method with Zn(II)TAP as passivation agents and ethanol as solvent.

Synthesis of C225-PCQDs.

Poly(ethylene glycol) diamine $(H_2NCH_2(CH_2CH_2O)_n CH_2NH_2$ (n=35, MW≈1500, PEG1500N)) was used to react with PCQDs for surface passivation (FIG. 18). In a typical reaction, PEG1500N (200 mg, 0.13 mmol) was mixed with 20 mg PCQDs in 20 mL DI water, and the mixture was refluxed for 72 h at 120° C. with the presence of nitrogen gas. After the reaction, the mixture was cooled to room temperature and dispersed in water, followed by centrifugation for 30 min. The supernatant was collected and purified by dialysis membrane (MW ~3500) in DI water to yield $NH_2$-PCQDs. Covalent binding of cetuximab to the $NH_2$-PCQDs was performed using a modification of the standard EDC-NHS reaction. Typically, 80 μL of cetuximab solution was dissolved in 2 mL of phosphate buffered saline (PBS) (pH=7.4) solution, followed by the addition of 4 mg EDC and 5 mg sulf-NHS for activation at 4° C. for 15 min. 20 mg of $NH_2$-PCQDs in 5 mL PBS (pH=7.4) were added and the mixed solution was allowed to react at 4° C. for 12 h. The resulting suspension was centrifuged for 10 min to remove weight precipitate, and then was dialyzed against DI water for three days at 4° C. The C225-PCQDs was lyophilized and re-dissolved in phosphate buffer (pH 7.4) for further characterization and application.

Single Oxygen Detection.

2',7'-dichlorofluorescin diacetate (DCFH-DA) was recrystallized from ethanol and stored frozen. To convert DCFH-DA to dichlorofluorescin, 0.5 ml of 1 mM DCFH-DA in ethanol was added to 2 ml of 0.01 N NaOH and allowed to sit at room temperature for 30 min. The hydrolysate was then neutralized with 10 ml of 25 mM sodium phosphate buffer at pH 7.4, and stored on ice in the dark until use. The final concentration of DCFH alkali activated solution was 40 mM. Fluorescence spectra of DCF solutions were recorded in 508-600 nm emission range under excitation at 488 nm. Irradiation of activated DCFH solutions in the presence of porphyrin-based nanodots results in the transformation of non-fluorescent activated into highly fluorescent 2',7'-dichlorofluorescein with emission peak at 525 nm.

Confocal Laser Scanning Microscope Studies.

Cellular uptake by cancer cells was examined using a confocal laser scanning microscope (CLSM). Cancer cells were seeded in 6-well culture plates (a sterile cover slip was put in each well) at a density of $5 \times 10^4$ cells per well and allowed to adhere for 24 h. After that, the cells were treated with porphyrin carbon quantum dots (0.5 mg/mL) for 12 h at 37° C. After that, the supernatant was carefully removed and the cells were washed three times with PBS. Subsequently, the slides were mounted and observed by confocal microscope (Zeiss Laser Scanning Confocal Microscope; LSM7 DUO) using ZEN 2009 software (Carl Zeiss).

Subcellular Localization.

Cancer cells were cultured in Minimum Essential Medium (MEM) containing 10% fetal bovine serum and 1% antibiotics penicillin and streptomycin (P/S) and incubated at 37° C. in a humidified 5% $CO_2$ atmosphere. Cancer cells ($6 \times 10^3$ cells per well) were seeded in 96-well plates and incubated overnight at 37° C. in a humidified 5% $CO_2$ atmosphere. After being rinsed with PBS (pH 7.4), the cells were incubated with porphyrin carbon quantum dots at a concentration of 0.5 mg/mL for 12 h at 37° C. in the dark under the same conditions. The cells were rinsed with PBS again, and stained by LysoTracker® Green DND-26 for 30 min. After the cells were fixed with 4% paraformaldehyde, DAPI (Invitrogen) was used to mount each coverslip on a glass slide for confocal laser scanning microscope (CLSM).

In Vitro PDT Effect.

To compare the dark toxicity and phototoxicity of the porphyrin carbon quantum dots, the stock solutions of nanomedicines were diluted with fresh medium to various concentrations (5, 10, 20, 50 and 100 μg/mL). The cells were then incubated with these solutions at 37° C. in 5% $CO_2$ for 4 h, and the cultures were then irradiated using a 500 W Xe lamp as the light source with an intensity of 6.5 mW/cm² for 0 or 30 min before removing the porphyrin carbon quantum dots solution and adding fresh medium. Subsequently, the plates were incubated at 37° C. in 5% $CO_2$ for 24 h. The cell medium solutions were exchanged for 100 μL of fresh medium, followed by the addition of L of CCK8 solution to each well. The culture plates were then incubated at 37° C. in 5% $CO_2$ for 4 h. The absorbance of an untreated cell population under the same experimental conditions was used as the reference point to establish 100% cell viability. The absorbance of the 96-well plates was detected by a 450 nm laser by a Plate reader (1420 Multi-label Counter Perkin Elmer).

INDUSTRIAL APPLICABILITY

The present invention relates to a development of a biocompatible and red emissive cetuximab-conjugated porphyrin carbon quantum dots (C225-PCQDs) that precisely target the non-small lung cancer cells and lead to a remarkable photodynamic therapy (PDT), demonstrating its high potential for targeted imaging and PDT of non-small lung cancer. The results show that C225-PCQDs can selectively accumulate in cancer cells with over-expression of EGFR and be used as an effective platform for simultaneous imaging and targeted PDT of cancer.

What we claim:

1. A nanoparticle comprising a carbon matrix and one or more moieties present on the surface of the carbon matrix, wherein the one or more moieties is selected from the group consisting of —$CO_2H$ and —C(=O)NH($CH_2CH_2O)_n$$CH_2CH_2NHR$, wherein n is a whole number selected from 3-100 and R is a hydrogen or a targeting group; and the carbon matrix comprises a compound of Formula I:

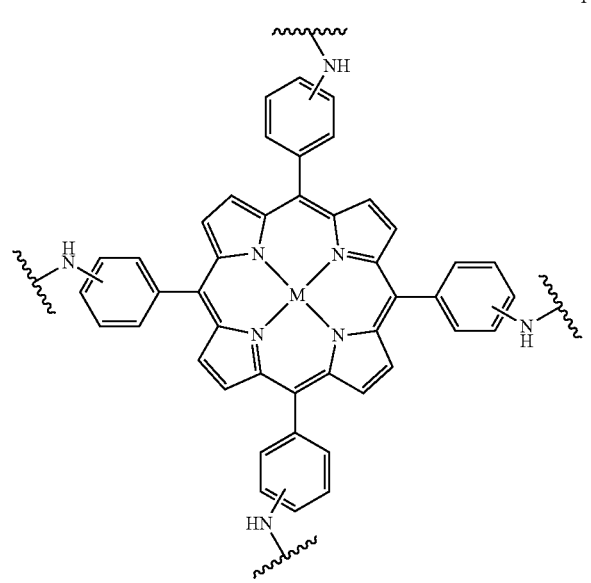

wherein, M is a metal selected from the group consisting of Co, Ni, Mn, Zn, Pt, and Pd;
or M represents two hydrogen, each of which is covalently bound to a nitrogen; and

represents a covalent nitrogen-carbon bond between the compound of Formula I and the carbon matrix.

2. The nanoparticle of claim 1, wherein n is a whole number selected from 3-40.

3. The nanoparticle of claim 1, wherein the nanoparticle has an average diameter of about 3 to about 3.5 nm.

4. The nanoparticle of claim 1, wherein the carbon matrix comprises graphitic carbon.

5. The nanoparticle of claim 1, wherein the targeting group is selected from the group consisting of an antibody, an antibody fragment, a peptide, an aptamer, and a small molecule.

6. The nanoparticle of claim 5, wherein the antibody is cetuximab or panitumumab; the peptide is a cyclic RGD peptide; and the aptamer is anti-nucleolin aptamer AS1411.

7. The nanoparticle of claim 1, wherein the nanoparticle has an average diameter of about 3 to about 3.5 nm; n is whole number selected from 3-40; the carbon matrix comprises graphitic carbon; M is Zn; or M represents two hydrogen, each of which is covalently bound to a nitrogen; and R is cetuximab.

8. A method for treating non-small cell lung cancer in a patient in need thereof, comprising the step of administering a therapeutically effective amount of the nanoparticle of claim 7 to the patent.

9. A method for imaging a cell that overexpresses epidermal growth factor receptor (EGFR), comprising the step of contacting the cell with the nanoparticle of claim 7 and detecting the fluorescence of the nanoparticle of claim 7.

10. A method of synthesizing the nanoparticle of claim 1, comprising the steps of:
a) contacting an organic acid selected from the group consisting of aspartic acid, citric acid, ethylenediaminetetraacetic acid (EDTA), glutamic acid, and tartaric acid with a compound of Formula II:

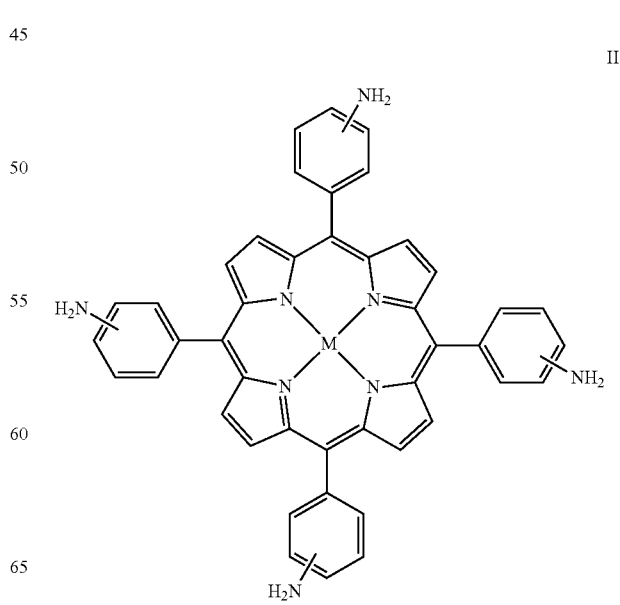

wherein, M is a metal selected from the group consisting of Co, Ni, Mn, Zn, Pt, and Pd; or M represents two hydrogen, each of which is covalently bound to a nitrogen; thereby forming a polymerized polyamide;

b) subjecting the polymerized polyamide to hydrothermal carbonization thereby forming an unfunctionalized nanoparticle comprising a carbon matrix and one or more —$CO_2H$ present on the surface of the carbon matrix; and the carbon matrix comprises a compound of Formula I:

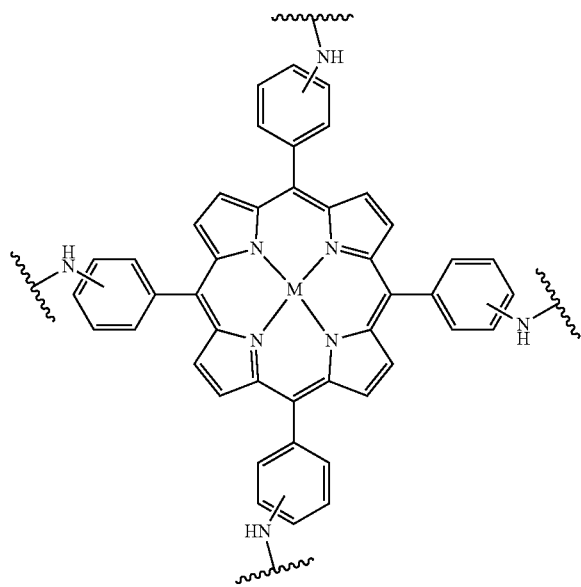

wherein, M is a metal selected from the group consisting of Co, Ni, Mn, Zn, Pt, and Pd; or M represents two hydrogen, each of which is covalently bound to a nitrogen; and

represents a covalent nitrogen-carbon bond between the compound of Formula I and the carbon matrix;

c) contacting the unfunctionalized nanoparticle with $NH_2(CH_2CH_2O)_nCH_2CH_2NH_2$, wherein n is a whole number selected from 3-100, under conditions for forming an amide bond, thereby forming an amine terminated nanoparticle; and d) optionally contacting the amine terminated nanoparticle with a targeting group comprising an activated carbonyl thereby forming the nanoparticle of claim 1.

11. The method of claim 10, wherein the step of contacting the compound of Formula II and the organic acid, the compound of Formula II and organic acid are present in a mass to mass ratio of about 1:10 to about 5:15 of the compound of Formula II to the organic acid.

12. The method of claim 10, wherein the organic acid is citric acid.

13. The method of claim 10, wherein n is a whole number selected from 3-40.

14. The method of claim 13, wherein the step of contacting the contacting the unfunctionalized nanoparticle with $NH_2(CH_2CH_2O)_nCH_2CH_2NH_2$, the unfunctionalized nanoparticle and $NH_2(CH_2CH_2O)_nCH_2CH_2NH_2$ are present in a mass to mass ratio of about 1:4 to about 5:95 the unfunctionalized nanoparticle to the $NH_2(CH_2CH_2O)_nCH_2CH_2NH_2$.

15. A nanoparticle made according to the method of claim 14.

16. The method of claim 10, wherein the targeting group is selected from the group consisting of an antibody, an antibody fragment, a peptide, an aptamer, and a small molecule.

17. The method of claim 10, further comprising the step of purifying the unfunctionalized nanoparticle by dialysis.

18. The method of claim 10, wherein the hydrothermal carbonization is conducted at a temperature between about 160° C. to about 240° C.

19. The method of claim 10, wherein the nanoparticle has an average diameter of about 3 to about 3.5 nm; n is whole number selected from 3-40; the carbon matrix comprises graphitic carbon; M is Zn; or M represents two hydrogen, each of which is covalently bound to a nitrogen; and the targeting group comprising an activated carbonyl is cetuximab comprising an activated carbonyl.

20. A nanoparticle made according to the method of claim 19.

\* \* \* \* \*